United States Patent
Chen

(10) Patent No.: US 12,324,642 B2
(45) Date of Patent: Jun. 10, 2025

(54) ROBOTIC ARM FOR MINIMALLY INVASIVE SURGERY

(71) Applicant: Eabmed Science and Technology (Shanghai) Co., Ltd., Shanghai (CN)

(72) Inventor: Yi Chen, Shanghai (CN)

(73) Assignee: Eabmed Science and Technology (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 18/703,923

(22) PCT Filed: Oct. 13, 2022

(86) PCT No.: PCT/CN2022/125098
§ 371 (c)(1),
(2) Date: Apr. 23, 2024

(87) PCT Pub. No.: WO2023/082928
PCT Pub. Date: May 19, 2023

(65) Prior Publication Data
US 2024/0415586 A1 Dec. 19, 2024

(30) Foreign Application Priority Data
Nov. 12, 2021 (CN) .......................... 202111339224.1

(51) Int. Cl.
*A61B 34/30* (2016.01)
*A61B 34/00* (2016.01)

(52) U.S. Cl.
CPC ........ *A61B 34/30* (2016.02); *A61B 2034/302* (2016.02); *A61B 2034/715* (2016.02)

(58) Field of Classification Search
None
See application file for complete search history.

(56) References Cited

U.S. PATENT DOCUMENTS

2007/0173976 A1* 7/2007 Schena ................. A61B 34/70
700/263
2011/0282359 A1* 11/2011 Duval .................... H04N 23/60
606/130

(Continued)

FOREIGN PATENT DOCUMENTS

| CN | 102764157 A | 11/2012 |
|----|-------------|---------|
| CN | 107468293 A | 12/2017 |

(Continued)

OTHER PUBLICATIONS

Faraz , A "A robotic case study: optimal design for laparoscopic positioning stands", Proceedings of International Conference on Robotics and Automation Feb. 28, 1997 p. 1554.

*Primary Examiner* — Martin T Ton
(74) *Attorney, Agent, or Firm* — Woodard, Emhardt, Henry, Reeves & Wagner, LLP

(57) ABSTRACT

A robotic arm for minimally invasive surgery, comprising: a support mechanism, with a support base and a distal end connected by a movable connector; a posture adjustment mechanism with a rotation and pitching member rotatably connected to the distal end. The end of the rotation and pitching member is rotatably provided with an instrument base. A first rotation axis of the rotation and pitching member and a second rotation axis of the instrument base intersect at the remote center of motion. The rotation and pitching member drives the instrument base to pitch. An instrument driving mechanism is connected to the instrument base to install and drive surgical instruments. The robotic arm adopts a single-arm structure and is suitable for minimally invasive surgeries such as single-port or few-port surgeries. Flexible and free spatial posture adjustment like deflection, pitching, and rolling of the instrument base are achieved.

19 Claims, 27 Drawing Sheets

(56) References Cited

U.S. PATENT DOCUMENTS

| | | | |
|---|---|---|---|
| 2017/0086927 A1* | 3/2017 | Auld | A61B 34/30 |
| 2017/0086928 A1 | 3/2017 | Auld et al. | |
| 2018/0243048 A1* | 8/2018 | Shan | A61B 8/466 |
| 2018/0318020 A1* | 11/2018 | Thompson | A61B 34/70 |
| 2019/0142540 A1 | 5/2019 | Chow | |
| 2020/0238542 A1* | 7/2020 | Castro | B25J 18/007 |

FOREIGN PATENT DOCUMENTS

| | | |
|---|---|---|
| CN | 108042208 A | 5/2018 |
| CN | 209464087 U | 10/2019 |
| CN | 110680505 A | 1/2020 |
| CN | 111163905 A | 5/2020 |
| CN | 111166471 A | 5/2020 |
| CN | 111700654 A | 9/2020 |
| CN | 213606561 U | 7/2021 |
| CN | 114098978 A | 3/2022 |

\* cited by examiner

ROBOTIC ARM FOR MINIMALLY INVASIVE SURGERY

FIELD OF THE DISCLOSURE

The present invention relates to the technical field of surgical robots, and specifically to a robotic arm used for minimally invasive surgery.

BACKGROUND

In robot-assisted minimally invasive surgeries, robotic arms are mainly used to hold surgical instruments instead of doctors and perform surgical operations accurately and stably under the surgeon's control. Most of the existing robots used for minimally invasive surgery have a multi-arm architecture and are suitable for multi-port minimally invasive endoscopic surgeries.

However, surgeries involving narrow passages such as thoracic surgeries, gynecological surgeries, and urological surgeries are single-port or few-port minimally invasive surgeries. If existing surgical robots are used, problems such as multiple robotic arms interfering with each other and limited working space are likely to occur, causing the surgical robots to be unable to function normally, and even causing damage to the patient's skin incision. In addition, the freedom of movement of the existing surgical robots cannot be flexibly adjusted, and does not meet the precise operation requirements of minimally invasive surgeries such as single-port or few-port surgeries.

It should be noted that the information disclosed in the background section above is only used to enhance understanding of the background of the present invention, and therefore may include information that does not constitute prior arts known to those of ordinary skill in the art.

SUMMARY OF THE INVENTION

In view of this, the present invention provides a robotic arm for minimally invasive surgery, which adopts a single-arm structure and is suitable for minimally invasive surgeries such as single-port or few-port surgeries, and has a pose adjustment function, especially two rotation and pitching functions provided by the posture adjustment mechanism, enabling flexible and free spatial posture adjustment movements, such as deflection, pitching and rolling of the instrument base relative to the remote center of motion.

One aspect of the present invention provides a robotic arm for minimally invasive surgery, comprising: a support mechanism, comprising a support base, and a distal end connected to the support base through a movable connector; and, a posture adjustment mechanism, comprising a rotation and pitching member rotatably connected to the distal end of the support mechanism, wherein, an instrument base is rotatably connected to an distal end of the rotation and pitching member, and, a first rotation axis of the rotation and pitching member intersects with a second rotation axis of the instrument base at a remote center of motion, and the rotation and pitching member is configured at least to drive the instrument base to perform a pitching movement relative to the remote center of motion; and, an instrument driving mechanism, connected to the instrument base and used to install and drive one or more surgical instruments.

In some embodiments, the rotation and pitching member comprises: a rotation base, connected to the distal end of the support mechanism through a first rotation joint, wherein the first rotation joint has a vertical rotation axis constituting the first rotation axis; and, a pitching assembly, with a proximal end movably connected to the rotation base and a distal end connected to the instrument base through a second rotation joint, wherein a rotation axis of the second rotation joint constitutes the second rotation axis.

In some embodiments, the pitching assembly comprises: a pitch drive rod, with a first end connected to the rotation base through a first rotation mechanism; and, a first connecting rod, with a first end connected to a second end of the pitch drive rod through a second rotation mechanism; and, a second connecting rod, with a first end connected to a second end of the first connecting rod through a third rotation mechanism, and with a second end connected to the instrument base; wherein, the second rotation mechanism is parallel to and synchronously linked with the first rotation mechanism and the third rotation mechanism respectively; and when the first rotation mechanism drives the pitch drive rod to rotate, the second rotation mechanism drives the first connecting rod to translate, wherein an angle between the first connecting rod and the first rotation axis remains unchanged, and, the second rotation mechanism and the third rotation mechanism drive the second connecting rod to swing, wherein an angle between the second connecting rod and the pitch drive rod remains unchanged.

In some embodiments, the first rotation mechanism comprises a first winch fixed on the rotation base, and an actuation shaft fixed on the first end of the pitch drive rod, wherein the actuation shaft is rotatably located at a center of the first winch; and, the second rotation mechanism comprises a second winch fixed on the first end of the first connecting rod, and a third winch rotatably connected to the second end of the pitch drive rod, wherein the second winch and the third winch share a passive shaft; and, the third rotation mechanism comprises a fourth winch fixed on the first end of the second connecting rod, and the fourth winch is rotatably connected to the second end of the first connecting rod, wherein a passive shaft of the fourth winch is parallel to the passive shaft of the second winch and the third winch as well as to the actuation shaft; and, the first winch, the second winch, the third winch, and the fourth winch are synchronously connected through coupling cables respectively.

In some embodiments, the rotation base is configured as an L-shaped base, and an outer wall of a horizontal arm of the L-shaped base is connected to the support mechanism; and, the pitching assembly is connected to an inner wall of a vertical arm of the L-shaped base, and rotation axes of the first rotation mechanism, the second rotation mechanism and the third rotation mechanism are all configured as horizontal rotation axes.

In some embodiments, the rotation base is configured as an arc-shaped base; and, the pitching assembly comprises: a plurality of arc-shaped rods connected in sequence, wherein, a proximal end of the plurality of arc-shaped rods is connected to the arc-shaped base through an arc-shaped guide rail, and the arc-shaped rods are connected through arc-shaped guide rails, and a distal end of the plurality of arc-shaped rods is connected to the instrument base.

In some embodiments, the plurality of arc-shaped rods comprises a first arc-shaped rod connected to the arc-shaped base, and a second arc-shaped rod connected to the instrument base, wherein projections of the arc-shaped base, the first arc-shaped rod and the second arc-shaped rod on a vertical plane are arcs and have a same radius of curvature.

In some embodiments, the rotation and pitching member comprises: a fixed base, fixed to the distal end of the support mechanism; and, a rotation and pitching chain, comprising a drive rod connected to the fixed base through a proximal rotation actuator, and a passive rod group connected to the drive rod through a passive rotation joint; wherein, the proximal rotation actuator has a vertical rotation axis, which constitutes the first rotation axis, and, a distal end of the passive rod group is connected to the instrument base through a distal rotation actuator, and a rotation axis of the distal rotation actuator constitutes the second rotation axis.

In some embodiments, the rotation and pitching chain has a plurality of parallel branch chains, and each of the branch chains comprises a said drive rod and a said passive rod group connected to each other.

In some embodiments, the rotation and pitch chain comprises: a first branch chain, comprising a first drive rod connected to the fixed base through a first proximal rotation actuator, and a first passive rod group connected to the first drive rod through a first passive rotation joint, wherein the first passive rod group comprises a plurality of first passive rods connected through passive rotation joints; and, a second branch chain, comprising a second drive rod connected to the fixed base through a second proximal rotation actuator, and a second passive rod group connected to the second drive rod through a second passive rotation joint, wherein the second passive rod group comprises a plurality of second passive rods connected through passive rotation joints; wherein, the first proximal rotation actuator and the second proximal rotation actuator are coaxial with the first rotation axis and are configured to be actuated jointly or independently, and the distal end of the first passive rod group and the distal end of the second passive rod group are jointly connected to the instrument base through the distal rotation actuator.

In some embodiments, the first passive rod group comprises two first passive rods and the second passive rod group comprises two second passive rods, and, a proximal first passive rod of the first passive rod group and a proximal second passive rod of the second passive rod group are connected through an intermediate rotation axis, wherein the intermediate rotation axis intersects with the first rotation axis.

In some embodiments, projections on a vertical plane of the first drive rod, of each of the first passive rods, of the second drive rod, and of each of the second passive rods are all arcs with a same radius of curvature.

In some embodiments, the instrument driving mechanism comprises a plurality of instrument driving modules arranged in a parallel configuration, which are respectively connected to the instrument base through a plurality of installation mechanisms, and the installation mechanisms are configured to drive the instrument driving modules to move perpendicular and/or parallel to a plane of the instrument base, and movement paths of the instrument driving modules do not interfere with each other.

In some embodiments, sequentially arranged along a second direction parallel to the plane of the instrument base, the installation mechanism comprises: an installation base, fixed to the instrument base; and, a forward and backward drive unit, movably connected to the installation base and movably connected with a forward and backward pallet, wherein the forward and backward drive unit is configured to move along a first direction perpendicular to the plane of the instrument base and to drive the forward and backward pallet along the first direction; and, a translation drive unit, fixedly connected to the forward and backward pallet and movably connected to a translation pallet, wherein the translation drive unit is configured to drive the translation pallet to move in the second direction, and the instrument drive module is fixedly connected to the translation pallet.

In some embodiments, the forward and backward driving unit comprises: a forward and backward drive motor, equipped with a first transmission gear set; and, a first lead screw and a second lead screw, respectively with opposite rotation directions, and arranged side by side along the first direction; wherein a proximal end of the first lead screw is connected in a matching manner to the installation base, and a proximal end of the second lead screw is connected in a matching manner to the forward and backward pallet, and a distal end of the first lead screw and a distal end of the second lead screw are driven by the first transmission gear set; and, when the forward and backward driving motor rotates forward, the first lead screw drives the forward and backward driving unit to move forward in the first direction, and the second lead screw drives the forward and backward pallet to move forward in the first direction; and, when the forward and backward driving motor reverses, the first lead screw drives the forward and backward driving unit to move backward along the first direction, and the second lead screw drives the forward and backward pallet to move backward along the first direction.

In some embodiments, the translation drive unit comprises: a translation drive motor, equipped with a second transmission gear set; and, a drive screw, arranged along the first direction and connected to a distal end of the second transmission gear set; and, a pair of fixed hinges, respectively fixed to the distal end of the drive screw and a distal end of a slide rail provided at the translation pallet along the first direction; and, a pair of movable hinges, respectively connected to the proximal end of the drive screw and the proximal end of the slide rail; wherein the pair of fixed hinges and the pair of movable hinges are connected by a pivotable X-shaped support; and, when the translation drive motor drives the drive screw to rotate, the movable hinges respectively move along the drive screw and the slide rail, and the X-shaped support pivots, and the translation pallet moves along the second direction.

In some embodiments, the movable connector comprises: a vertical support rod, connected to the support base through a first sliding joint, wherein the first sliding joint is configured to drive the vertical support rod to move vertically; and, a planar rod assembly, connected to the vertical support rod through a first bearing rotation joint, wherein the first bearing rotation joint is configured to drive the planar rod assembly to rotate in a plane perpendicular to the vertical support rod, and a distal end of the planar rod assembly constitutes the distal end of the support mechanism.

In some embodiments, the planar rod assembly comprises: a first rod, connected to the vertical support rod through the first bearing rotation joint, and, a second rod, connected through a second bearing rotation joint to the first rod; or, the planar rod assembly comprises: a third rod, connected to the vertical support rod through the first bearing rotation joint, and, a fourth rod, connected to the third rod through a second sliding joint.

In some embodiments, the first sliding joint, the second sliding joint, the first bearing rotation joint, and the second bearing rotation joint are all equipped with an electric actuator which is equipped with a fail-safe mechanical brake, or a pneumatic actuator which is equipped with a fail-safe mechanical brake.

Compared with the prior arts, the beneficial effects of the present invention at least comprise:

The robotic arm of the present invention adopts a single-arm structure and is suitable for minimally invasive surgeries such as single-port or few-port surgeries to avoid problems such as movement interferences and limited operating space. Through the pose adjustment function, especially the two rotation and pitching movements provided by the posture adjustment mechanism, flexible and free spatial posture adjustment movements such as deflection, pitching and rolling of the instrument base relative to the remote center of motion can be achieved, meeting the precise operation requirements of minimally invasive surgeries such as single-port or few-port surgeries. The remote center of motion is configured as the posture adjustment reference point, which may correspond to the incision point on the patient's body surface during the surgeries, so as to adjust the spatial pose of the robotic arm based on the posture adjustment reference point, and to avoid contact and influence of the robotic arm on the posture adjustment reference point during the spatial posture adjustment movements.

It should be understood that the above general description and the following detailed description are exemplary and explanatory only, and do not limit the present invention.

BRIEF DESCRIPTION OF THE DRAWINGS

The accompanying drawings, which are incorporated in and constitute a part of this specification, illustrate embodiments consistent with the invention and together with the description serve to explain the principles of the invention. Obviously, the drawings described below are only some embodiments of the present invention. For those of ordinary skill in the art, other drawings can be obtained based on these drawings without exerting creative efforts.

DESCRIPTION OF THE ILLUSTRATED EMBODIMENTS

Figure 1:
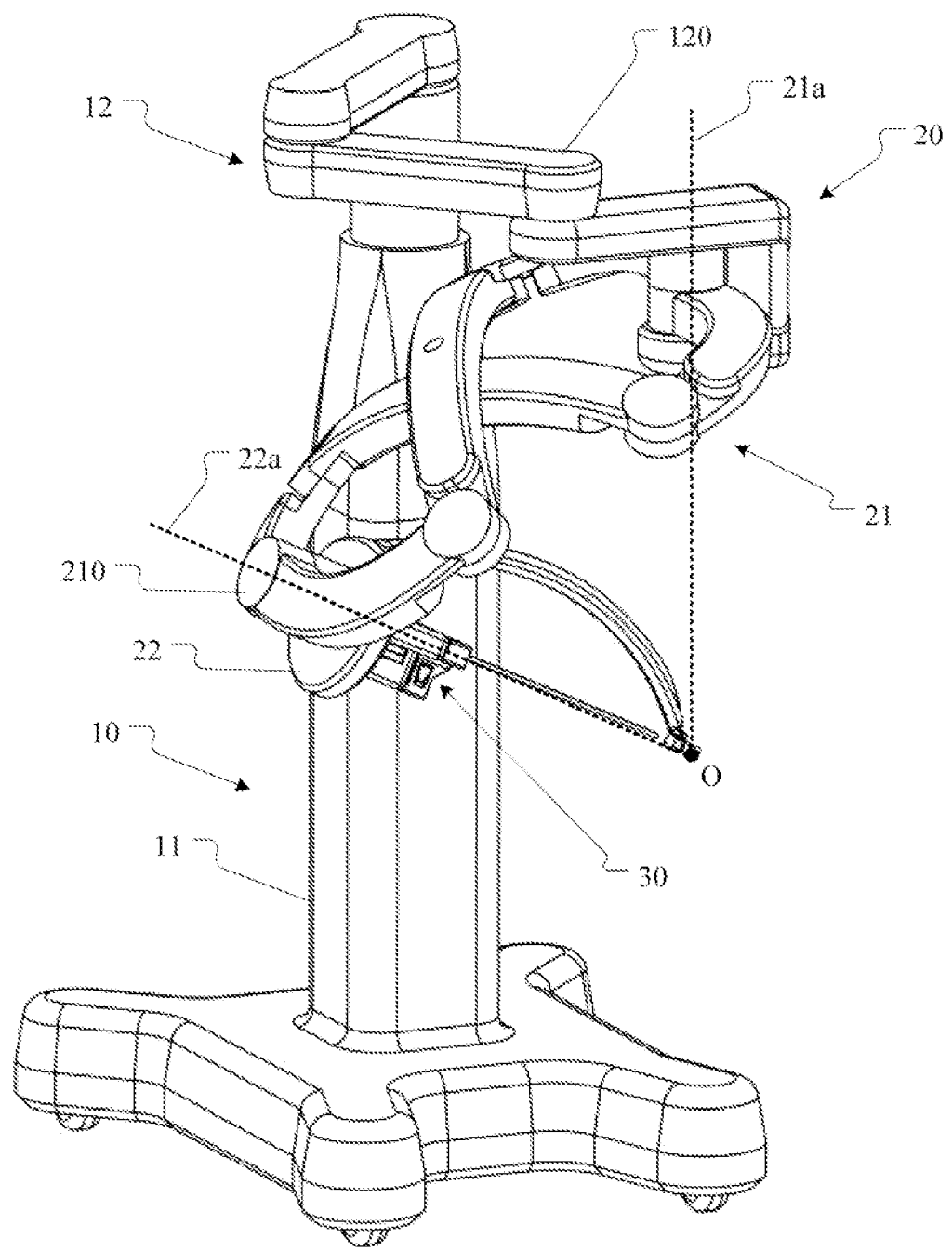
FIG. 1 shows a schematic three-dimensional structural diagram of a robotic arm in an embodiment of the present invention.

Example embodiments will now be described more specifically with reference to the accompanying drawings. Example embodiments may, however, be implemented in various forms and should not be construed as limited to the embodiments set forth herein. Rather, these embodiments are provided so that this disclosure will be thorough and complete, and will fully convey the concept of example embodiments to those skilled in the art.

The drawings are merely schematic illustrations of the invention and are not necessarily drawn to scale. The same reference numerals in the drawings represent the same or similar parts, and thus their repeated description will be omitted. Some of the block diagrams shown in the FIGS. are functional entities and do not necessarily correspond to physically or logically separate entities. These functional entities may be implemented in form of software, or implemented in one or more hardware modules or integrated circuits, or implemented in different networks and/or processor devices and/or microcontroller devices.

The use of "first", "second" and similar words in specific descriptions does not imply any order, quantity or importance, but is only used to distinguish different components. It should be noted that, as long as there is no conflict, the embodiments of the present invention and features in different embodiments can be combined with each other.

FIG. 1 shows the three-dimensional structure of a robotic arm in an embodiment. Referring to FIG. 1, the robotic arm for minimally invasive surgery in this embodiment comprises a support mechanism 10, comprising a support base 11 and a distal end 120 connected to the support base 11 by a movable connector 12. The robotic arm further comprises a posture adjustment mechanism 20, which comprises a rotation and pitching member 21, rotatably connected to the distal end 120 of the support mechanism 10. The distal end 210 of the rotation and pitching member 21 is rotatably connected with an instrument base 22. The first rotation axis 21a of the component 21 intersects with the second rotation axis 22a of the instrument base 22 at the remote center of motion O. The rotation and pitching member 21 can drive the instrument base 22 to perform pitching movement relative to the remote center of motion O. An instrument driving mechanism 30 is connected to the instrument base 22 and is used for installing and driving surgical instruments.

The above-mentioned robotic arm adopts a single-arm architecture, which is suitable for minimally invasive surgeries such as single-port or few-port surgeries, and can avoid problems such as movement interference and limited operating space. Through the posture adjustment function, especially the rotation and pitching movements provided by the posture adjustment mechanism 20, flexible and free spatial posture adjustment movements such as deflection, pitching and rolling of the instrument base relative to the remote center of motion can be achieved, meeting the precise operation requirements of minimally invasive surgeries such as single-port or few-port surgeries. The remote center of motion corresponds to the posture adjustment reference point during the operation, thereby adjusting the spatial posture of the robotic arm according to the posture adjustment reference point can be achieved, so that touching and affecting the posture adjustment reference point during space posture adjustment movements of the robotic arm can be prevented.

The support mechanism 10, the posture adjustment mechanism 20, and the instrument driving mechanism 30 are respectively described in detail below.

FIG. 2 to FIG. 5 show the three-dimensional structure of the support mechanism in different embodiments. As shown in FIG. 2 to FIG. 5, the support base 11 is specifically a trolley base. The trolley base is mainly used to support the entire robotic arm, and the casters 110 at the bottom provide mobility. During preoperative preparation, the trolley base can be moved to a suitable position in the operation room and be anchored to the ground by locking the casters 110 to achieve stable fixation throughout the entire operation. The movable connector is mainly used to position the posture adjustment mechanism 20 to a suitable position related to the posture adjustment reference point during the preoperative preparation process. It is generally required, that the Z1 axis of the coordinate system X1-Y1-Z1 of the distal end 120 passes through the posture adjustment reference point. The driving of the movable connector can be manually controlled by a user or automatically controlled by the system.

Referring to FIG. 2 to FIG. 5, the movable connector specifically comprises: a vertical support rod 121, which is connected to the support base 11 through a first sliding joint (not specifically marked in the figure). The first sliding joint can drive the vertical support rod 121 to move vertically in a guide rail of the trolley base in the direction of arrow 1210. The planar rod assembly 122 is connected to the vertical support rod 121 through a first bearing rotation joint (not specifically marked in the figure). The first bearing rotation joint can drive the planar rod assembly 122 to rotate in a plane perpendicular to the vertical support rod 121 (as shown by arrow 1220). The end of the planar rod assembly 122 constitutes the distal end 120 of the load-support mechanism. By changing the rotation angle of the first bearing rotation joint, for the coordinate system X1-Y1-Z1 of the distal end 120, two degrees of freedom of movement in the X1-Y1 plane can be achieved. Combined with the degree of freedom provided by the first sliding joint in the Z1 direction, the distal end 120 has freedoms of movement in three directions in space relative to the trolley base, so that the posture adjustment mechanism 20 connected to the distal end 120 can be positioned to a suitable position relative to the patient.

The sliding joint is equipped with a linear actuator to drive the relevant components to perform linear motion. The rotation joint is equipped with a rotation actuator to drive the relevant components to rotate.

The planar rod assembly may comprise several rod segments that can rotate relative to each other, or may comprise several rod segments that can slide relative to each other.

Figure 2:
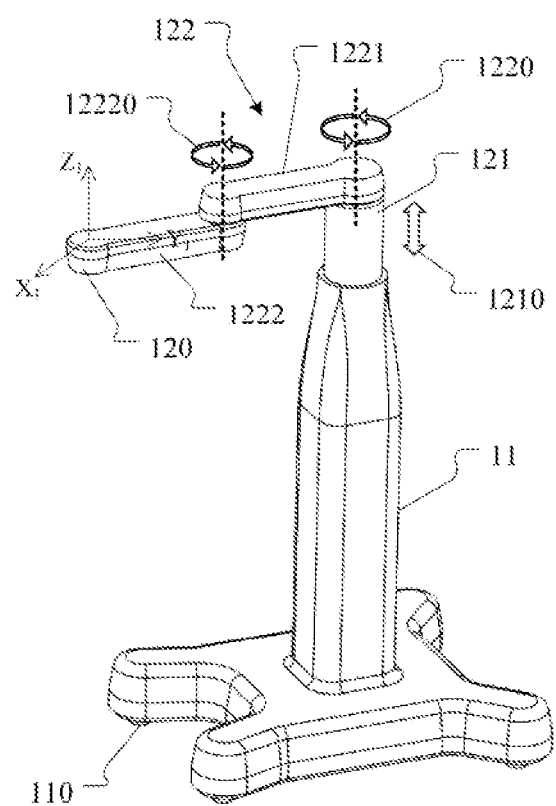
FIG. 2 and FIG. 3 show a schematic three-dimensional structural view of a planar rod assembly of the support mechanism in an embodiment of the present invention.
Figure 3:
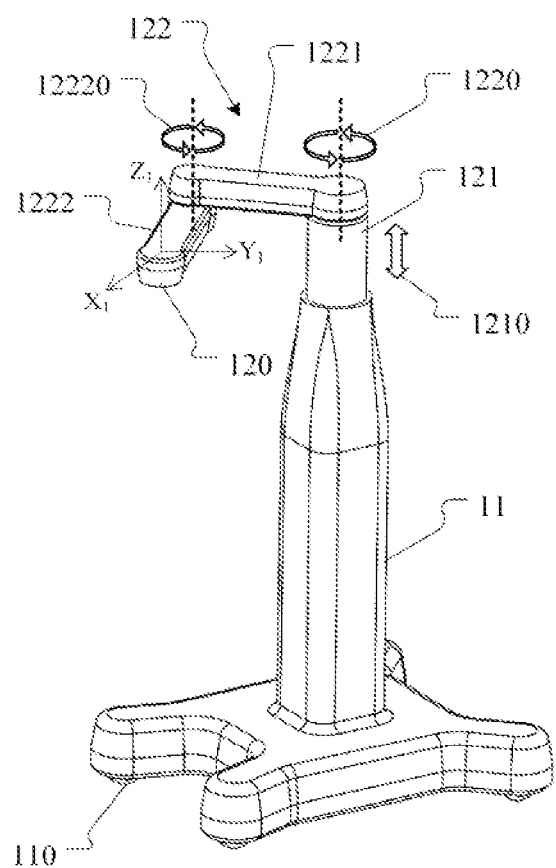

FIG. 2 and FIG. 3 show a three-dimensional structure of a planar rod assembly 122. Referring to FIG. 2 and FIG. 3, in this embodiment, the planar rod assembly 122 comprises: a first rod 1221 and a second rod 1222. The first rod 1221 is connected to the vertical support rod 121 by a first bearing rotation joint. The second rod 1222 is connected to the first rod 1221 through a second bearing rotation joint (not specifically marked in the figure), and the second bearing rotation joint can drive the second rod 1222 to rotate (such as indicated by arrow 12220). In this embodiment, by changing the rotation angles of the first bearing rotation joint and the second bearing rotation joint, two degrees of freedom of movement of the coordinate system X1-Y1-Z1 of the distal end 120 in the X1-Y1 plane can be achieved. And combined with the freedom of movement in the Z1 direction provided by the first sliding joint, the distal end 120 is enabled to move in three directions in space relative to the trolley base, thereby accurately positioning the posture adjustment mechanism 20 connected to the distal end 120 to a suitable position related to the patient.

Figure 4:
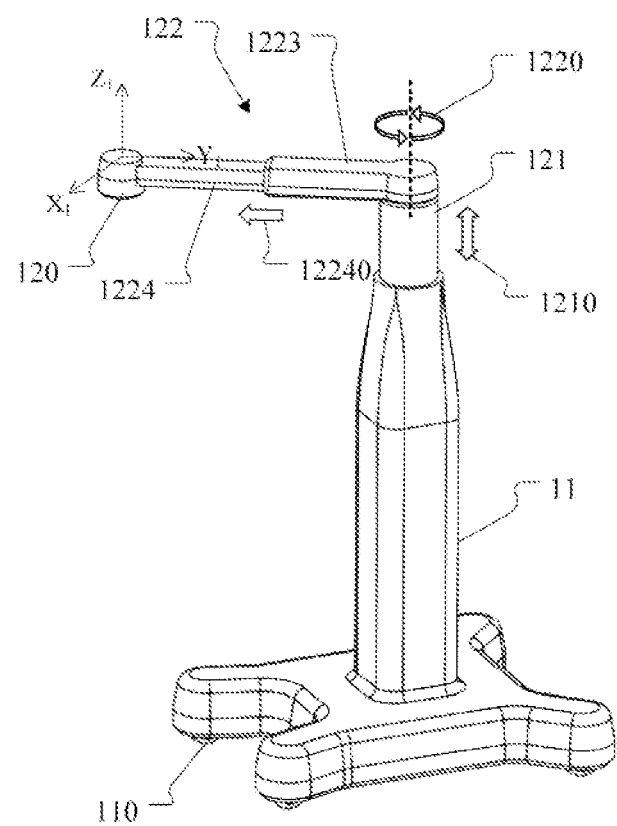
FIG. 4 and FIG. 5 show a schematic three-dimensional structural diagram of another planar rod assembly of the support mechanism in an embodiment of the present invention.
Figure 5:
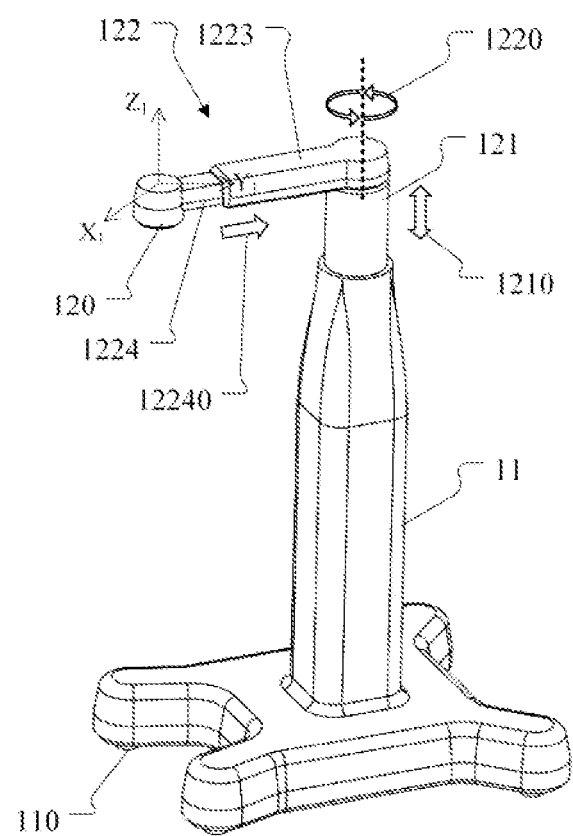

FIG. 4 and FIG. 5 show another three-dimensional structure of the planar rod assembly 122. Referring to FIG. 4 and FIG. 5, the planar rod assembly 122 in this embodiment comprises a third rod 1223 and a fourth rod 1224. The third rod 1223 is connected to the vertical support rod 121 through a first bearing rotation joint. The fourth rod 1224 is connected to the third rod 1223 through a second sliding joint (not specifically marked in the figure). And the second sliding joint can drive the fourth rod 1224 to perform linear motion (as shown by arrow 12240). In this embodiment, by changing the rotation angle of the first bearing rotation joint, combined with the movement of the second sliding joint, two degrees of freedom of movement of the coordinate system X1-Y1-Z1 of the distal end 120 in the X1-Y1 plane are achieved. And combined with degree of freedom in the Z1 direction provided by the first sliding joint, the distal end 120 is enabled to move in three directions in space relative to the trolley base, thereby accurately positioning the posture adjustment mechanism 20 connected to the distal end 120 to the appropriate position related to the patient.

In addition, for the movable connector 12, if there is no need to change the patient's position during the operation, the movable connector 12 is generally required to maintain the defined configuration throughout the entire process, and it must also be able to maintain the same configuration when the robotic arm system encounters unexpected situations such as power outage. Therefore, both the rotation actuators and the linear actuator in the movable connector 12 should be equipped with fail-safe mechanical brakes. Specifically, the above-mentioned first sliding joint, the second sliding joint, the first bearing rotation joint and the second bearing rotation joint are all equipped with electric actuators or pneumatic actuators with fail-safe mechanical brakes, to maintain the configuration of the movable connector 12 in an event of a system power outage.

The posture adjustment mechanism 20 is mainly used to adjust the spatial posture of surgical instruments during surgeries. In the case of single-port or few-port minimally invasive surgeries, the posture adjustment mechanism 20 achieves posture control of multiple parallel surgical instruments installed on the instrument base by adjusting the posture of the instrument base. The posture adjustment mechanism 20 has clinical requirements for precise adjustment during surgeries, and its motion control is generally achieved by an operator through master-slave control systems.

Figure 6:
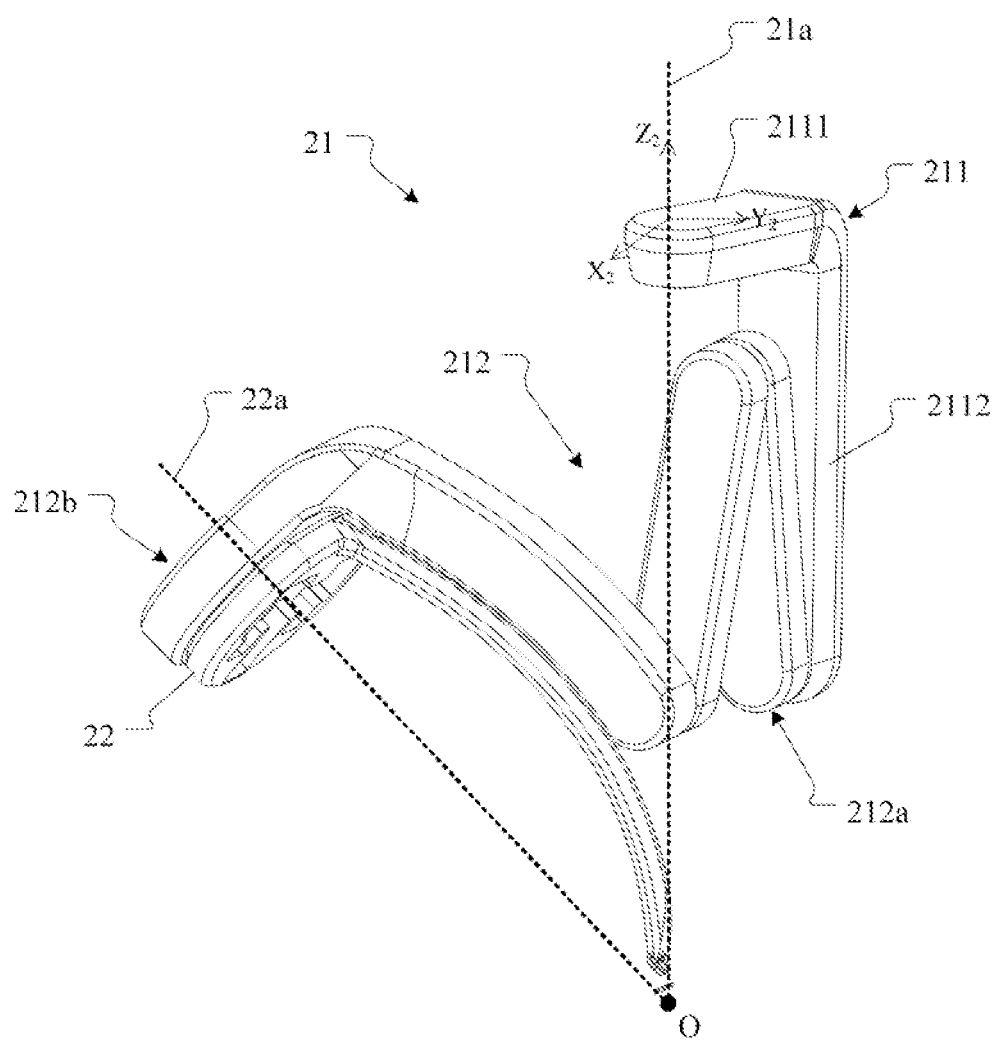
FIG. 6 shows a schematic three-dimensional structural diagram of a rotation and pitching member of the posture adjustment mechanism in an embodiment of the present invention.
Figure 11:
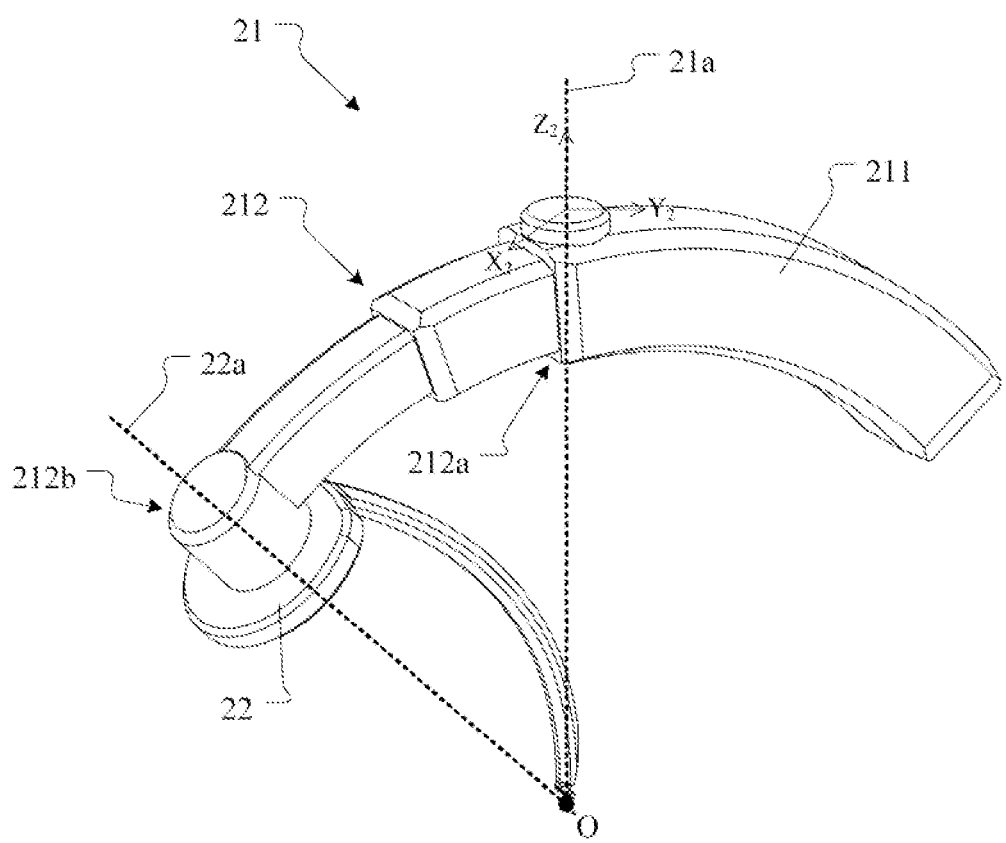
FIG. 11 shows a schematic three-dimensional structural diagram of another rotation and pitching member of the posture adjustment mechanism in an embodiment of the present invention.

FIG. 6 and FIG. 11 show the three-dimensional structure of the posture adjustment mechanism 20 in different embodiments. Referring to FIG. 6 and FIG. 11, the rotation and pitching member 21 of the posture adjustment mechanism 20 comprises a rotation base 211, which is connected to the distal end 120 of the support mechanism through the first rotation joint (not specifically indicated in the figure). The first rotation joint has a vertical rotation axis Z2, constituting a first rotation axis 21a. The end of the rotation base 211 that is connected to the distal end 120 of the support mechanism is configured with a node coordinate system X2-Y2-Z2. When assembling the rotation base 211 to the distal end 120 of the support mechanism, the node coordinate system X2-Y2-Z2 of the rotation base 211 can be aligned with the distal end coordinate system of the support mechanism. When the rotation base 211 is connected to the end coordinate system of the support mechanism through the rotation actuator, its vertical rotation axis Z2 coincides with the Z1 axis of the distal end coordinate system of the support mechanism and passes through the remote center of motion O. During minimally invasive surgeries, all movements of the robotic arm should ensure that the remote center of motion O is fixed relative to the patient's position. The rotation and pitching member 21 further comprises a pitching assembly 212. The pitching assembly 212 has a proximal end 212a, movably connected to the rotation base 211, and, a distal end 212b, connected to the instrument base 22 through a second rotation joint (not specifically marked in the figure). The rotation axis of the second rotation joint forms a second rotation axis 22a. The first rotation axis 21a and the second rotation axis 22a intersect at the remote center of motion O.

In the embodiment shown in FIG. 6, the rotation base 211 can be specifically configured as an L-shaped base. The outer wall of a horizontal arm 2111 of the L-shaped base is connected to the support mechanism, and the pitching assembly 212 is connected to an inner wall of a vertical arm 2112 of the L-shaped base.

Figure 7:
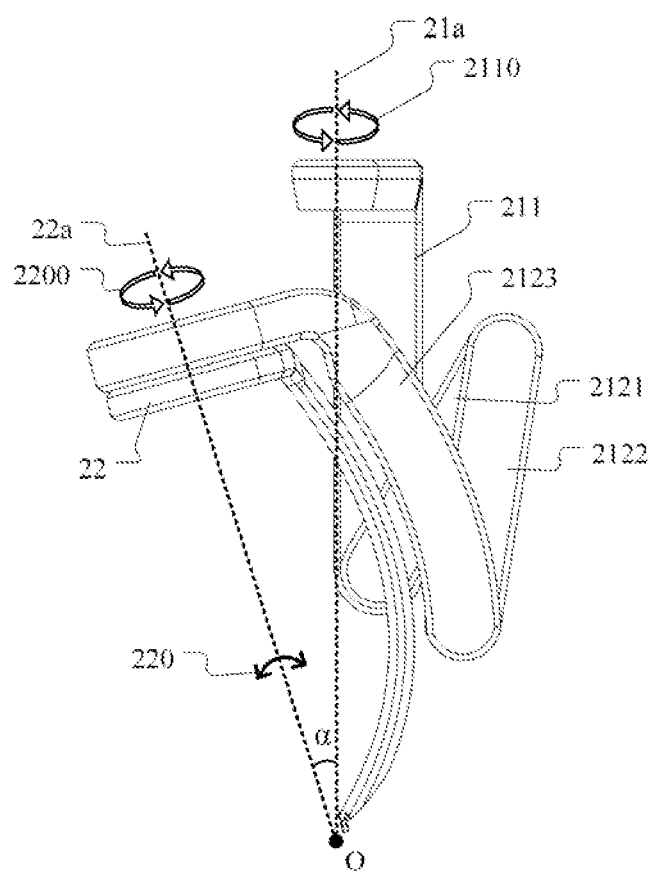
FIG. 7 and FIG. 8 show the front structural schematic diagram of the rotation and pitching member shown in FIG. 6 in two movement states.
Figure 8:
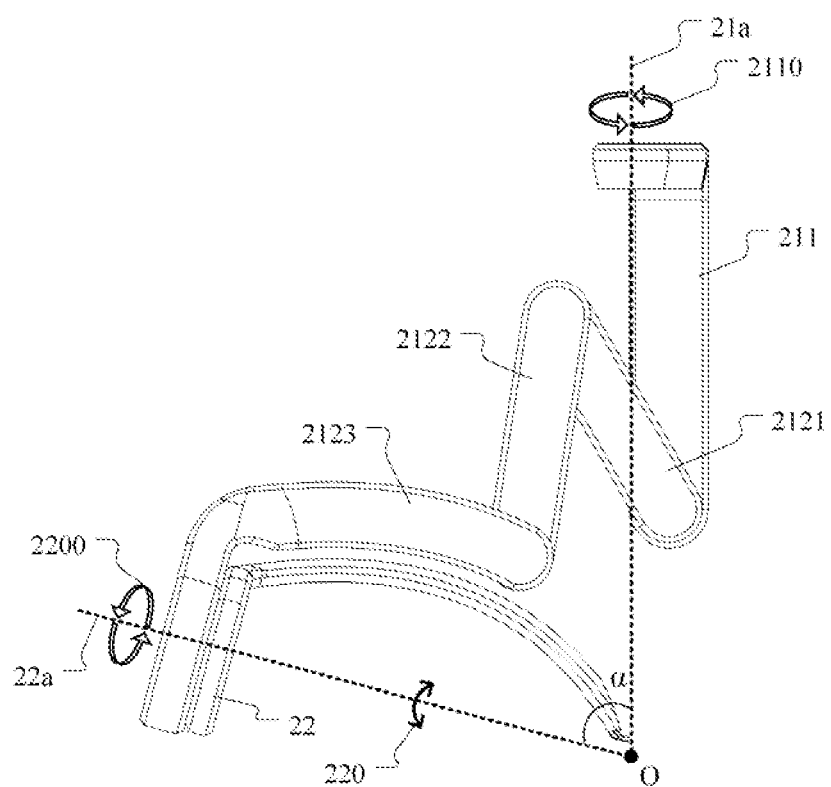

Referring to the front view structure of the rotation and pitching member 21 in two motion states shown in FIG. 6 to FIG. 8, in this embodiment, the pitching assembly 212 specifically comprises a pitch drive rod 2121, a first connecting rod 2122, and a second connecting rod 2123. The first end of the pitch drive rod 2121 is connected through a first rotation mechanism to the rotation base 211. The first rotation mechanism is equipped with a rotation actuator. The first end of the first connecting rod 2122 is connected to the second end of the pitch drive rod 2121 through a second rotation mechanism. The first end of the second connecting rod 2123 is connected to the second end of the first connecting rod 2122 through a third rotation mechanism, and the second end of the second connecting rod 2123 is connected to the instrument base 22. Wherein, the second rotation mechanism is parallel to the first rotation mechanism and the third rotation mechanism, and is synchronously linked with the first rotation mechanism and the third rotation mechanism respectively. When the first rotation mechanism drives the pitch drive rod 2121 to rotate, and the second rotation mechanism drives the first connecting rod 2122 to translate, the angle between the first connecting rod 2122 and the first rotation axis 21a remains unchanged. And, the second rotation mechanism and the third rotation mechanism drive the connecting rod 2123 to swing, while the angle between the second connecting rod 2123 and the pitch drive rod 2121 remains unchanged.

In this embodiment, as shown in FIG. 7 and FIG. 8, the pitch drive rod 2121, the first connecting rod 2122 and the second connecting rod 2123 are connected to constitute a parallel mapping mechanism. By changing the angle between the pitch drive rod 2121 and the first rotation axis 21a, the pitch angle α between the second rotation axis 22a and the first rotation axis 21a can be changed accordingly, so that the parallel mapping mechanism constituted by the pitch drive rod 2121, the first connecting rod 2122 and the second connecting rod 2123 is able to drive the instrument base 22 to make a pitching motion relative to the remote center of motion O (as shown by arrow 220). Moreover, the rotation actuator of the first rotation joint of the rotation base 211 is able to drive the rotation base 211 to rotate around the vertical rotation axis, that is, the first rotation axis 21a (as shown by arrow 2110), thereby driving the instrument base 22 relative to deflect relative to the remote center of motion O. In addition, the rotation actuator of the second rotation joint at the end of the pitching assembly 212 is able to drive the instrument base 22 to rotate around its rotation axis, that is, the second rotation axis 22a (as shown by arrow 2200), thereby causing the instrument base 22 to roll relative to the remote center of motion O. Through the above structure, the spatial posture adjustment movement of the instrument base 22 with three degrees of freedom of deflection, pitching and rolling with the remote center of motion O as a central fixed point can be achieved.

Figure 9:
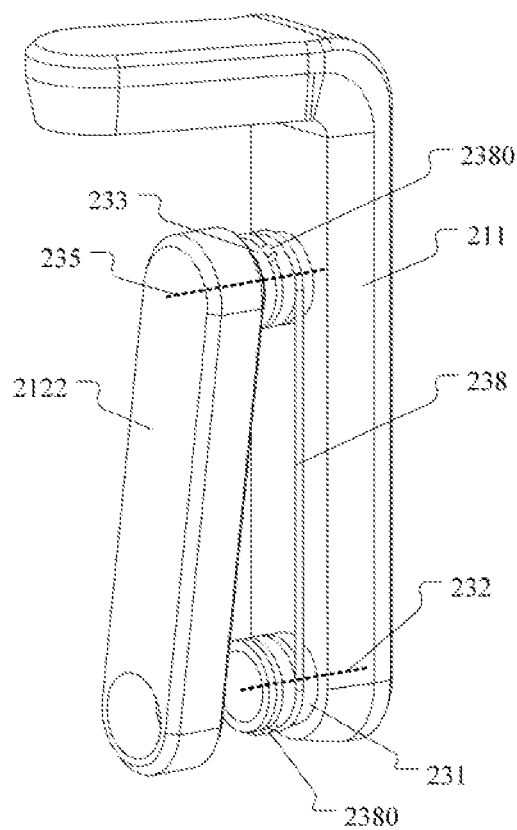
FIG. 9 and FIG. 10 show two partial structural schematic diagrams of the rotation and pitching member shown in FIG. 6.
Figure 10:
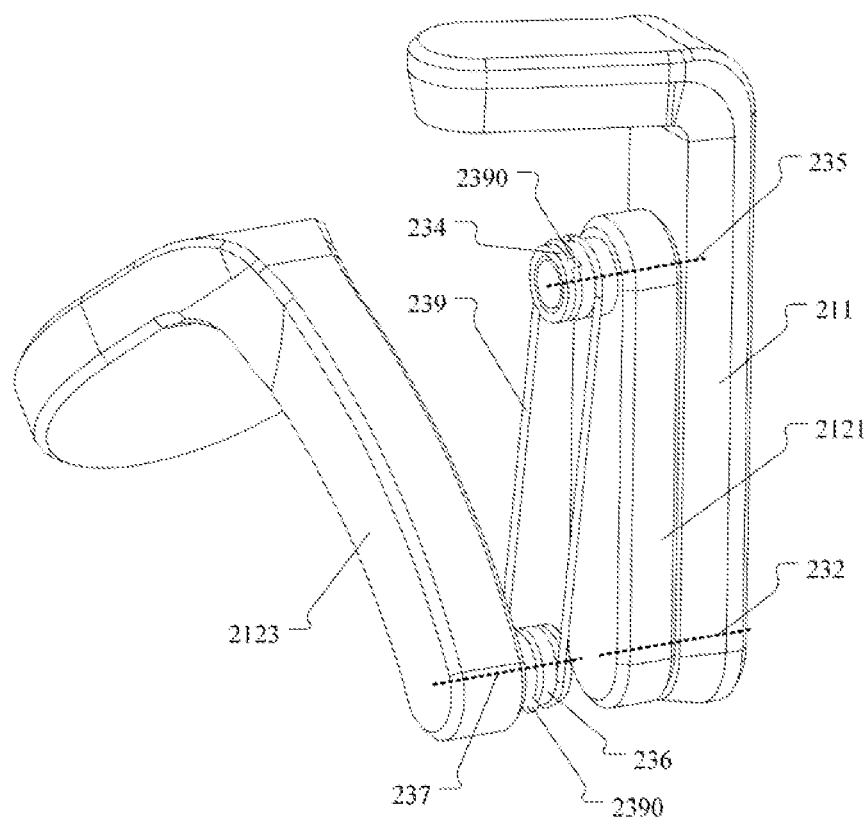

The specific principles of the parallel mapping mechanism are shown in FIG. 7 and FIG. 8, as well as with the two partial structures of the rotation and pitching member 21 shown in FIG. 9 and FIG. 10. The pitch drive rod 2121 is not shown in FIG. 9, and the first connecting rod 2122 is not shown in FIG. 10. The first rotation mechanism comprises: a first winch 231 fixed on the rotation base 211 and an actuation shaft 232 fixed on the first end of the pitch drive rod 2121. The actuation shaft 232 is rotatably provided at the center of the first winch 231. The second rotation mechanism comprises: a second winch 233 fixed on the first end of the first connecting rod 2122 and a third winch 234 rotatably connected to the second end of the pitch drive rod 2121. The second winch 233 and the third winch 234 share a passive shaft 235. The third rotation mechanism comprises a fourth winch 236 fixed on the first end of the second connecting rod 2123, and the fourth winch 236 is rotatably connected to the second end of the first connecting rod 2122. And a passive shaft 237 of the fourth winch 236 is parallel to the passive shaft 235 of the second winch 233 and the third winch 234, and parallel to the actuation shaft 232. And they are all horizontal axes. The first winch 231 and the second winch 233 are synchronously connected through two coupling cables 238, and the two coupling cables 238 are respectively fixed to the first winch 231 and to the second winch 233 through cable fixing pieces 2380. Thus, when the pitch drive rod 2121 is driven by a pitch actuator rotation shaft, that is, driven by the actuation shaft 232, and rotates around the actuation shaft 232, the second winch 233 revolves around the actuation shaft 232 while keeping itself from rotating, thereby maintaining the angle between the first connecting rod 2122 and the first rotation axis 21a remains unchanged. The third winch 234 and the fourth winch 236 are synchronously connected through two coupling cables 239, and the two coupling cables 239 are respectively fixed to the third winch 234 and to the fourth winch 236 through cable fixing pieces 2390. Thus, when the pitch drive rod 2121 is driven to rotate by the actuation shaft 232, the angle between the fourth winch 236 and the pitch drive rod 2121 remains unchanged, and thus the angle between the second connecting rod 2123 and the pitch drive rod 2121 remains unchanged. Using the above structure, by changing the angle between the pitch drive rod 2121 and the first rotation axis 21a, the pitching motion of the second connecting rod 2123 relative to the remote center of motion O as a central fixed point can be achieved. That means, a rotation of the actuation shaft 232 is parallelly mapped to the remote center of motion O.

Figure 12:
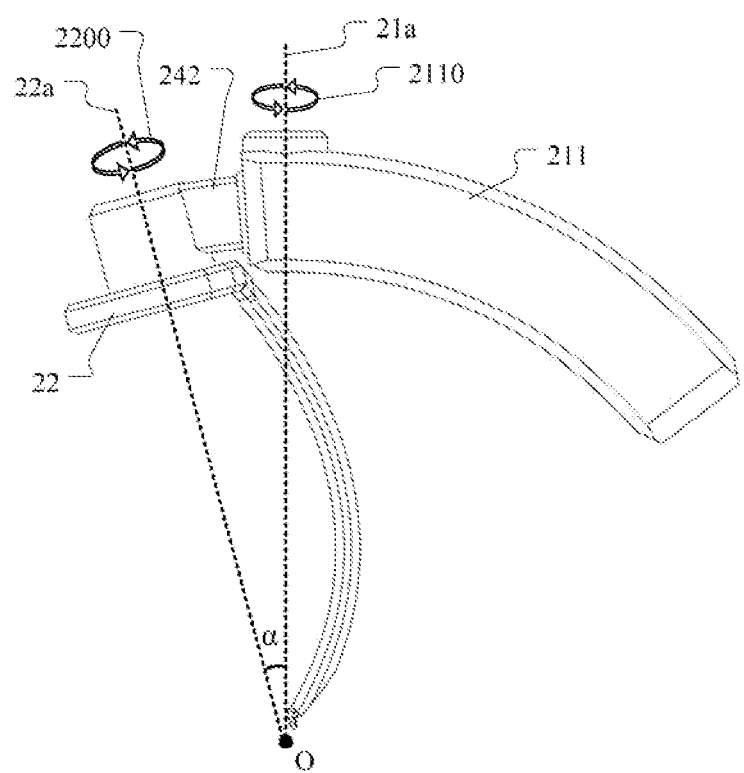
FIG. 12 and FIG. 13 show schematic side structural views of the rotation and pitching member shown in FIG. 11 in two movement states.
Figure 13:
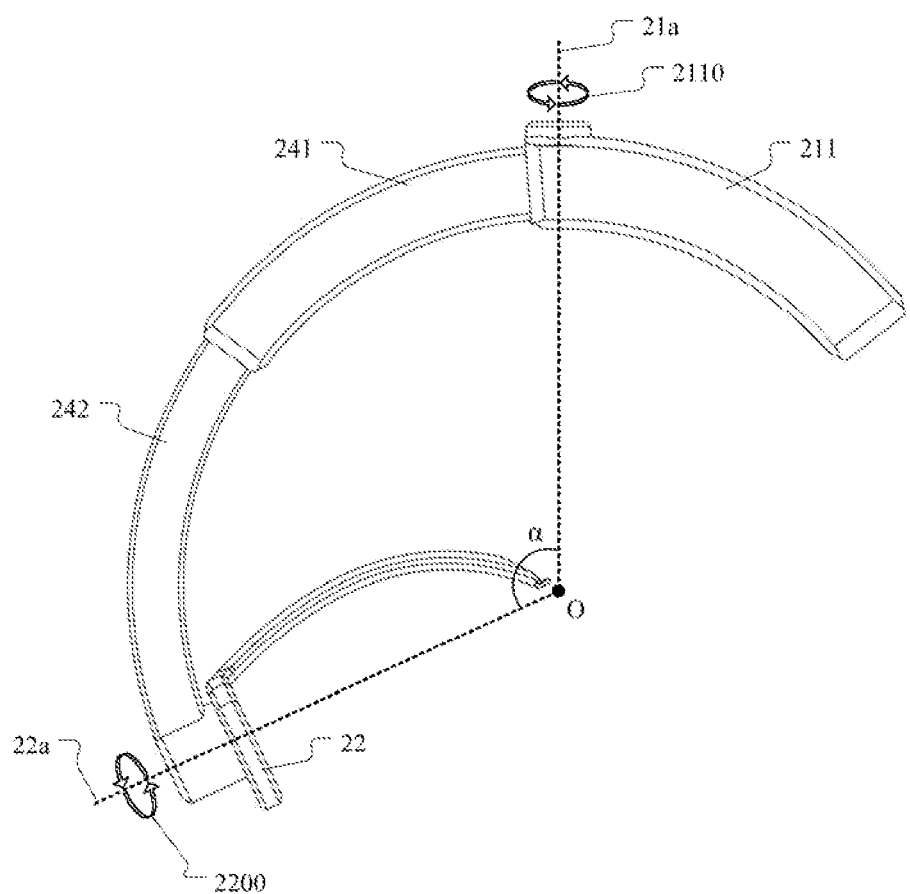

In the embodiment shown in FIG. 11, also referring to the side view structure of the rotation and pitching member 21 in two motion states shown in FIG. 12 and FIG. 13, the rotation base 211 is configured as an arc-shaped base. And the pitching assembly 212 comprises a plurality of arc-shaped rods connected in sequence. The proximal end of the plurality of arc-shaped rods, that is, the proximal end 212a of the pitching assembly 212, is connected to the arc-shaped base through an arc-shaped guide rail (not specifically marked in the figure). And the arc-shaped rods are connected through corresponding arc-shaped guide rails (not specifically marked in the figure). And the distal end, that is, the distal end 212b of the pitching assembly 212 is connected to the instrument base 22.

The plurality of arc-shaped rods may specifically comprise 2 arc-shaped rods, 3 arc-shaped rods or more. In this embodiment, the plurality of arc-shaped rods comprise a first arc-shaped rod 241 connected to the arc-shaped base and a second arc-shaped rod 242 connected to the instrument base 22. The projections of the arc-shaped base, the first arc-shaped rod 241 and the second arc-shaped rod 242 on a vertical plane are arcs and have a same radius of curvature.

In this embodiment, as shown in FIG. 11 to FIG. 13, the rotation base 211 is also aligned with the end coordinate system of the support mechanism through a node coordinate system X2-Y2-Z2. And the rotation base 211 is connected through a rotation joint and is driven to rotate by a rotation actuator. The first rotation axis 21a and the second rotation axis 22a intersect at a fixed remote center of motion O. The angle between the first rotation axis 21a and the second rotation axis 22a is called the pitch angle α. According to clinical requirements, the pitch angle α ranges from 10° to 120°. In this embodiment, the rotation actuator of the first rotation joint of the rotation base 211 is able to drive the rotation base 211 to rotate around the first rotation axis 21a (as shown by arrow 2110), driving the instrument base 22 to deflect relative to the remote center of motion O. The first arc-shaped rod 241 and the second arc-shaped rod 242 are able to drive the instrument base 22 to perform a pitching movement relative to the remote center of motion O through telescopic movements, thereby adjusting the pitch angle α. The rotation actuator of the second rotation pair at the end of the second arc-shaped rod 242 is able to drive the instrument base 22 to rotate around the second rotation axis 22a (as shown by arrow 2200), so that the instrument base 22 rolls relative to the remote center of motion O. Therefore, through the above structure, spatial posture adjustment movements of the instrument base 22 with the remote center of motion O as a central fixed point can be achieved, with three degrees of freedom: deflection, pitching, and rolling.

Figure 14:
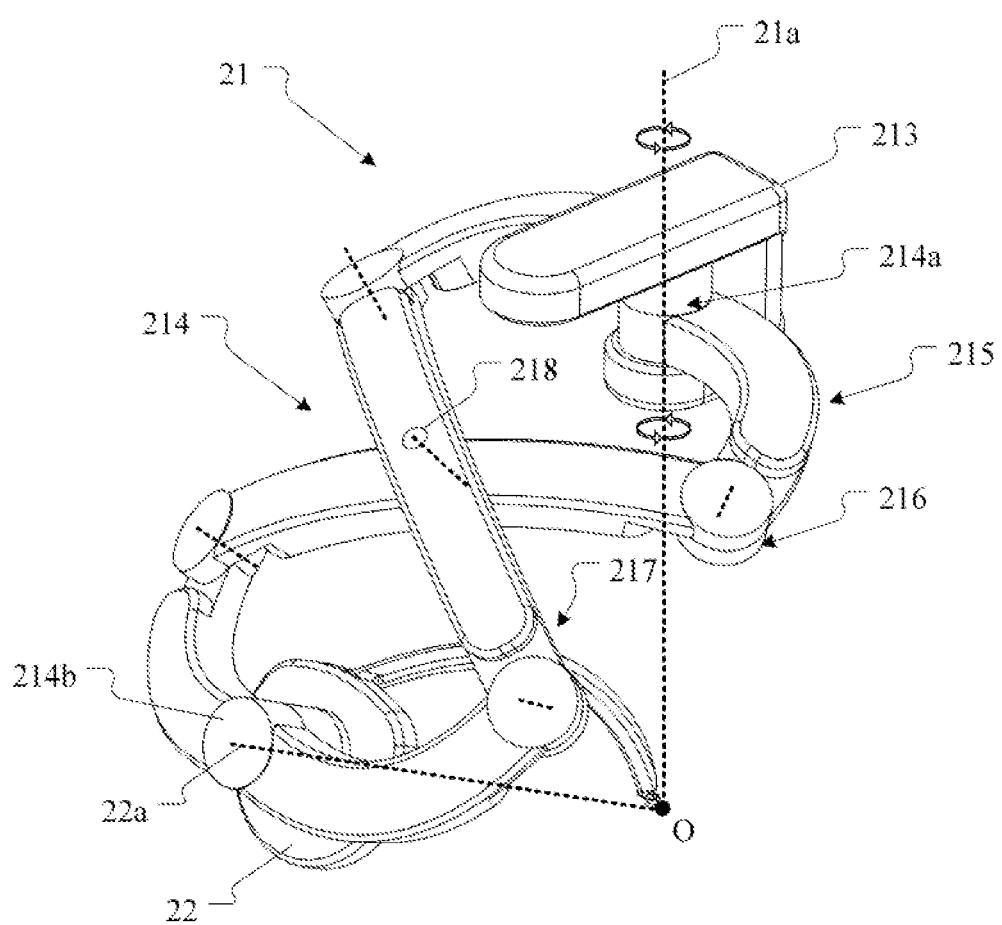
FIG. 14 shows a schematic three-dimensional structural diagram of another rotation and pitching member of the posture adjustment mechanism in an embodiment of the present invention.

FIG. 14 shows the three-dimensional structure of the rotation and pitching component of the posture adjustment mechanism 20 in another embodiment. Referring to FIG. 14, the rotation and pitching member 21 in this embodiment comprises a fixed base 213, which is fixed to the distal end of the support mechanism. An end of the fixed base 213 fixed to the distal end of the support mechanism is calibrated with a node coordinate system X3-Y3-Z3. The fixed base 213 can be assembled by aligning its node coordinate system X3-Y3-Z3 with the distal end coordinate system of the support mechanism. The rotation and pitching member 21 further comprises a rotation and pitching chain 214, which comprises a drive rod 215 connected to the fixed base 213 through a proximal rotation actuator 214a and a passive rod group 217 connected to the drive rod 215 through a passive rotation joint 216. The proximal rotation actuator 214a has a vertical rotation axis that constitutes the first rotation axis 21a. The distal end of the passive rod group 217 is connected to the instrument base 22 through a distal rotation actuator 214b. The rotation axis of the distal rotation actuator 214b constitutes the second rotation axis 22a. The first rotation axis 21a and the second rotation axis 22a also intersect at the remote center of motion O.

The rotation and pitching chain 214 may have multiple parallel branch chains, and each branch chain comprises a drive rod 215 and a passive rod group 217 connected to each other. In a basic design, the rotation and pitching chain 214 may comprise two parallel branch chains. In further optimized designs, the rotation and pitching chain 214 may comprise three or more parallel branch chains, thereby improving structural rigidity.

Figure 15:
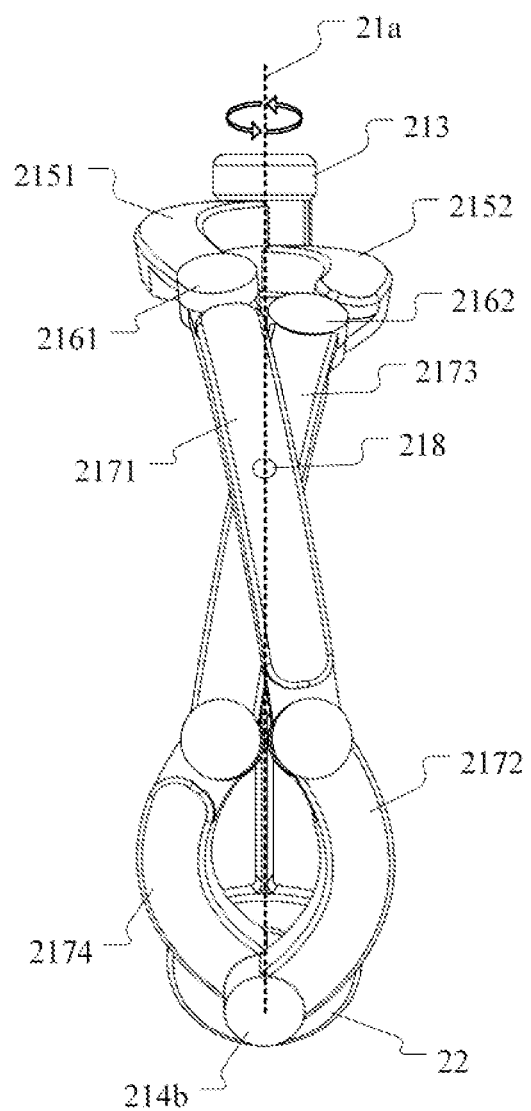
FIG. 15 shows a schematic front structural view of the rotation and pitching member shown in FIG. 14.
Figure 16:
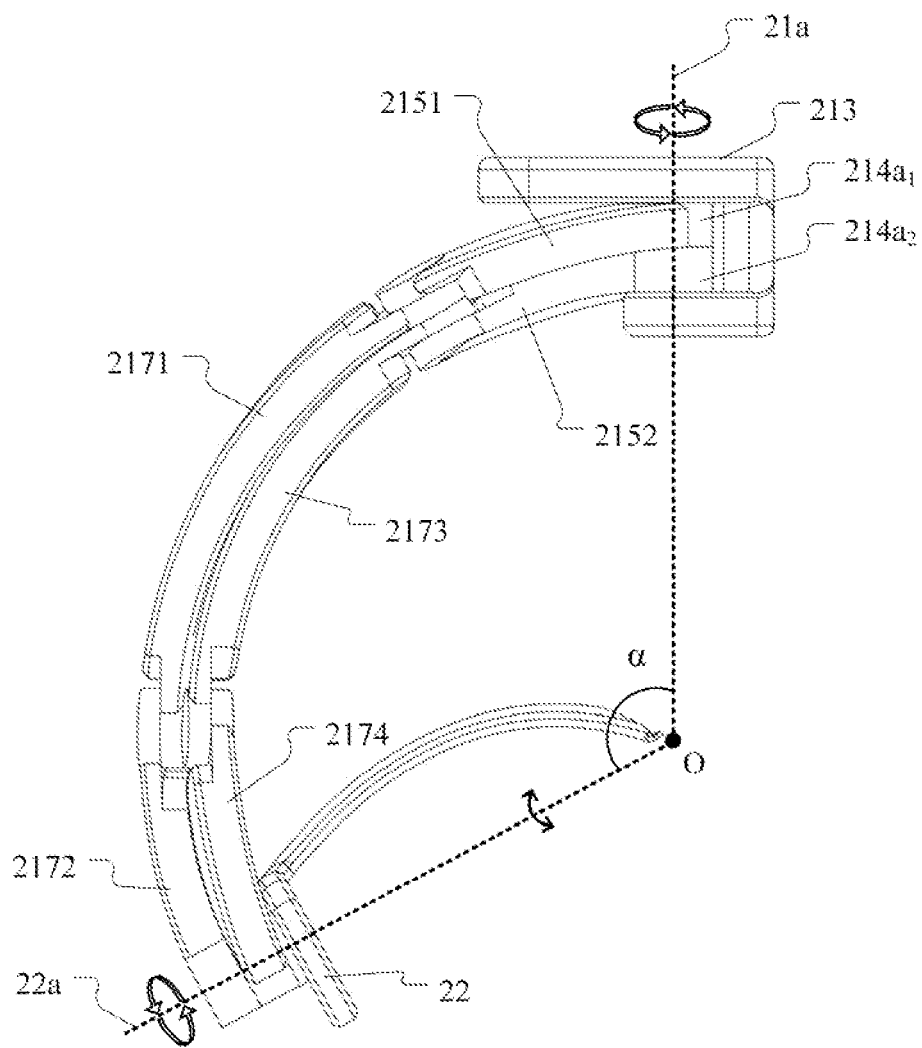
FIG. 16 shows a schematic side structural view of the rotation and pitching member shown in FIG. 14.
Figure 17:
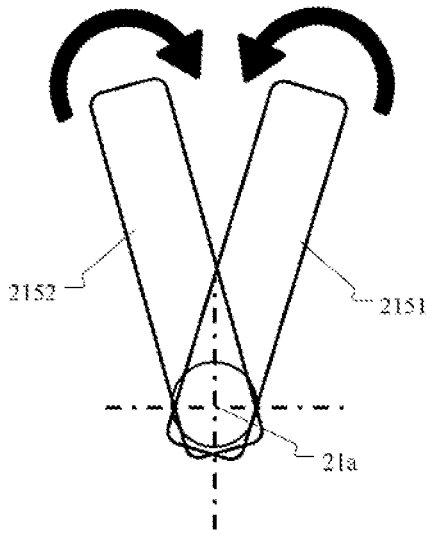
FIG. 17 to FIG. 20 show schematic diagrams of the movement principles of the two arms of the rotation and pitching member shown in FIG. 14.
Figure 18:
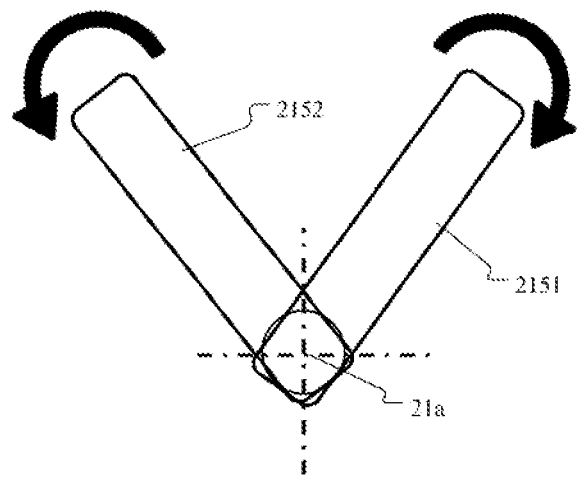
Figure 19:
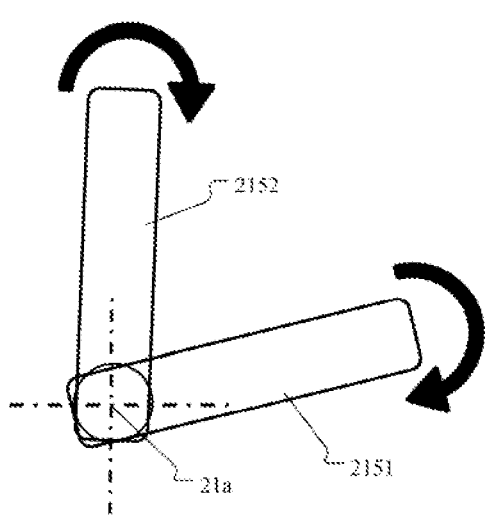
Figure 20:
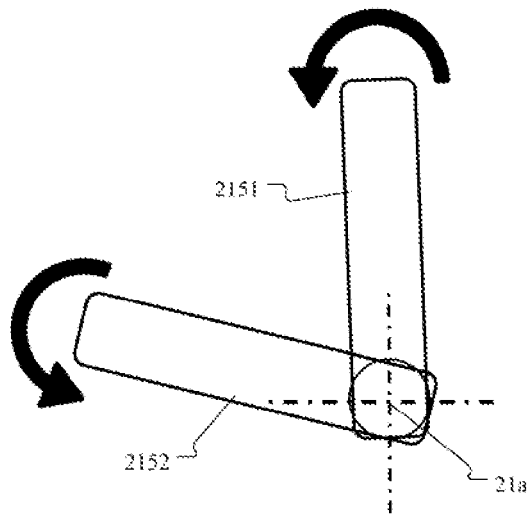

FIG. 15 shows the front view structure of the rotation and pitching member 21, and FIG. 16 shows the side view structure of the rotation and pitching member 21. As shown in FIG. 14 to FIG. 16, the rotation and pitching chain 214 in this embodiment comprises a first branch chain, comprising a first drive rod 2151 connected to the fixed base 213 through a first proximal rotation actuator 214a1, and a first passive rod group connected to the first drive rod 2151 through a first passive rotation joint 2161. The first passive rod group has a plurality of first passive rods connected through corresponding passive rotation joints. The rotation and pitching chain 214 further comprises a second branch chain, which comprises a second drive rod 2152 connected to the fixed base 213 through a second proximal rotation actuator 214a2, and a second passive rod group connected to the second drive rod 2152 through a second passive rotation joint 2162. The second passive rod group has a plurality of second passive rods connected through corresponding passive rotation joints. The first proximal rotation actuator 214a1 and the second proximal rotation actuator 214a2 are coaxially facing each other, and are coaxial with the first rotation axis 21a, and can be actuated jointly or independently, so that the first drive rod 2151 and the second drive rod 2152 rotate around the first rotation axis 21a together or independently. The distal end of the first passive rod group and the distal end of the second passive rod group are jointly connected to the instrument base 22 through the distal rotation actuator 214b. The first passive rod group may specifically comprise two first passive rods 2171 and 2172, which are connected through a passive rotation joint. The second passive rod group may specifically comprise two second passive rods 2173 and 2174, which are connected through a passive rotation joint. The proximal first passive rod 2171 of the passive rod group and the proximal second passive rod 2173 of the second passive rod group are connected through an intermediate rotation axis 218, which intersects with the first rotation axis 21a.

The posture adjustment mechanism 20 of this embodiment can be called a 2-RR (R) RR spherical parallel mechanism, wherein R is a rotation joint. The projections of the first drive rod, all the first passive rods, the second drive rod and all the second passive rods on a vertical plane are arcs and have a same radius of curvature. The rotation and pitching chain 214 comprises a first winch, wherein the first winch is fixed to the fixed base 213 and is coaxial with the proximal rotation actuator 214a; and, the passive rotation joint between the passive rod group 217 and the drive rod 215 comprises a second winch fixed on a proximal end of a first passive rod, and a third winch rotatably connected to a distal end of the drive rod 215, wherein the second winch and the third winch share a passive shaft; and, the passive rotation joint between the first passive rod and a second passive rod comprises a fourth winch fixed on a proximal end of the second passive rod, and the fourth winch is rotatably connected to the second end of the first passive rod, wherein a passive shaft of the fourth winch, the passive shaft of the second winch, and a shaft of the proximal rotation actuator 214a are respectively colinear with the remote center of motion O; and, the first winch, the second winch, the third winch, and the fourth winch are synchronously connected through coupling cables respectively.

FIG. 17 to FIG. 20 show the movement principle of the two branches of the rotation and pitching member 21. As shown in FIG. 16 to FIG. 20, the angle between the first rotation axis 21a and the second rotation axis 22a is called the pitching angle α. When the first proximal rotation actuator 214a1 drives the first drive rod 2151 to rotate counterclockwise, and the second proximal rotation actuator 214a2 drives the second drive rod 2152 to rotate clockwise by the same angle, the pitch angle α of the posture adjustment mechanism 20 increases. When the first proximal rotation actuator 214a1 drives the first drive rod 2151 to rotate clockwise, and the second proximal rotation actuator 214a2 drives the second drive rod 2152 to rotate counterclockwise at the same angle, the pitch angle α of the posture adjustment mechanism 20 decreases. When the first proximal rotation actuator 214a1 drives the first drive rod 2151, and the second proximal rotation actuator 214a2 drives the second drive rod 2152, both to rotate clockwise by a same angle, the deflection angle of the posture adjustment mechanism 20 increases in the clockwise direction. When the first proximal rotation actuator 214a1 drives the first drive rod 2151, and the second proximal rotation actuator 214a2 drives the second drive rod 2152, both to rotate counterclockwise by a same angle, the deflection angle of the posture adjustment mechanism 20 increases in the counterclockwise direction. The posture adjustment mechanism 20 of this embodiment can also achieve spatial posture adjustment movements with three degrees of freedom as the deflection, pitching, and rolling of the instrument base 22 relative to the remote center of motion O, where the first rotation axis 21a and the second rotation axis 22a intersect.

Figure 21:
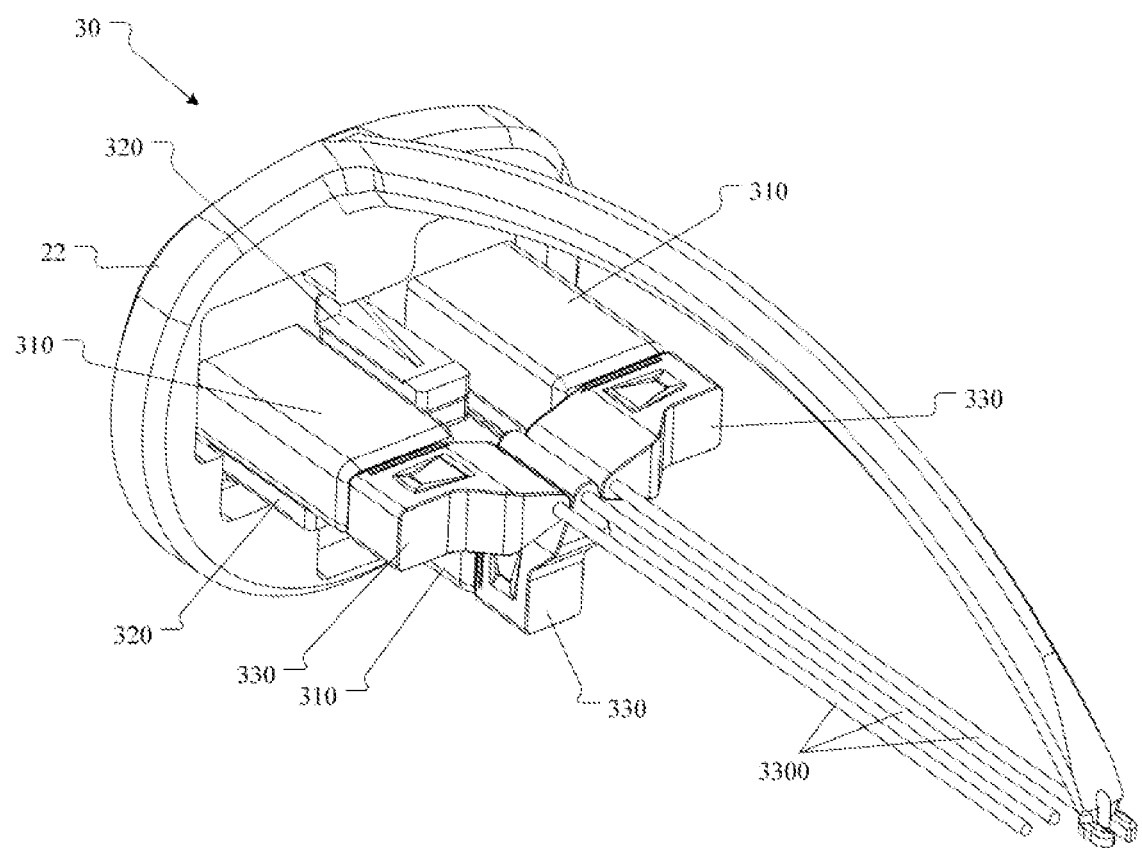
FIG. 21 shows a schematic three-dimensional structural diagram of the instrument driving mechanism in one embodiment of the present invention.

FIG. 21 shows the three-dimensional structure of the instrument driving mechanism in one embodiment. Referring to FIG. 21, the instrument driving mechanism 30 comprises a plurality of instrument driving modules 310 arranged side by side, which are connected to the instrument base 22 through multiple installation mechanisms 320. The installation mechanism 320 can drive the instrument driving module 310 to move perpendicularly and/or parallel to the plane of the instrument base 22, and the movement paths of the multiple instrument driving modules 310 do not interfere with each other. This embodiment comprises three instrument driving modules 310, but this is not limiting. The three instrument driving modules 310 are installed on the instrument base 22 respectively and are perpendicular to the main plane of the instrument base 22. Each instrument driving module 310 can dock with the surgical instrument 330 through a coupler and can keep the surgical instrument 330 relatively fixed during the operation. The functions of the instrument drive module 310 are: to ensure that the instrument shafts 3300 of multiple surgical instruments 330 are parallel to each other, and to connect and control the end effectors of the surgical instruments 330 by couplers to perform movement, posture adjustment and their combination in the patient's body. The instrument base 22 can be controlled by the posture adjustment mechanism 20, so that multiple parallel surgical instruments 330 can move in space relative to the posture adjustment reference point to form a specific spatial posture according to requirements. The installation mechanism 320 can provide the instrument drive module 310 with two degrees of freedom of spatial movement to manipulate the surgical instruments 330 or to manipulate instruments with specific predefined spatial configuration. When manipulating an instrument with specific predefined spatial configuration, touching or affecting the posture adjustment reference point can be avoided.

Figure 22:
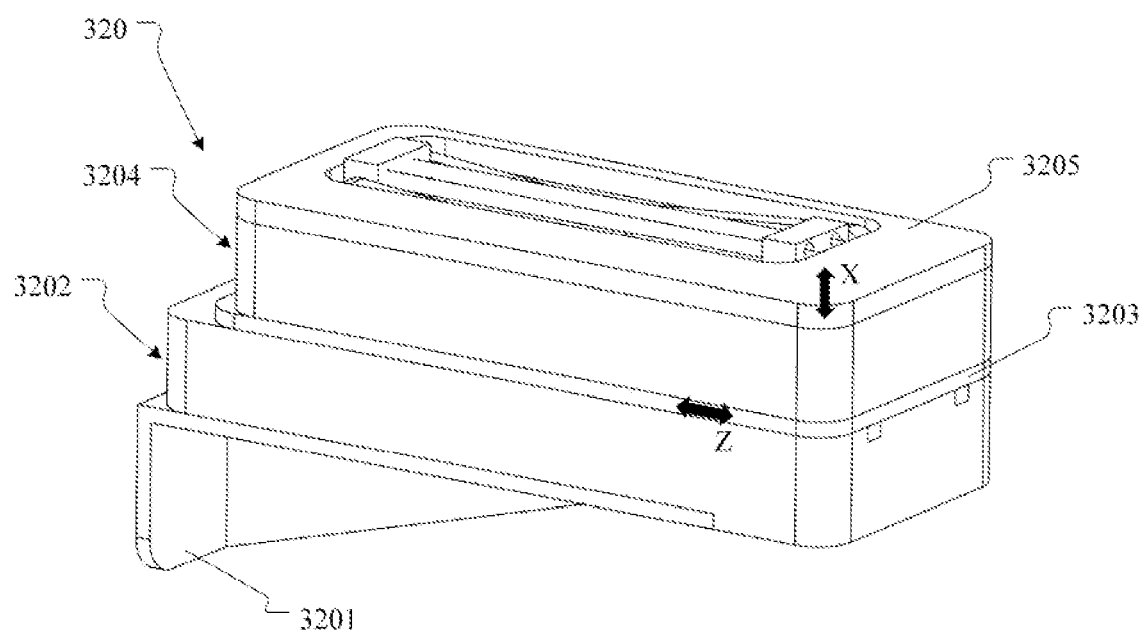
FIG. 22 shows a schematic three-dimensional structural diagram of the installation mechanism in an embodiment of the present invention.
Figure 23:
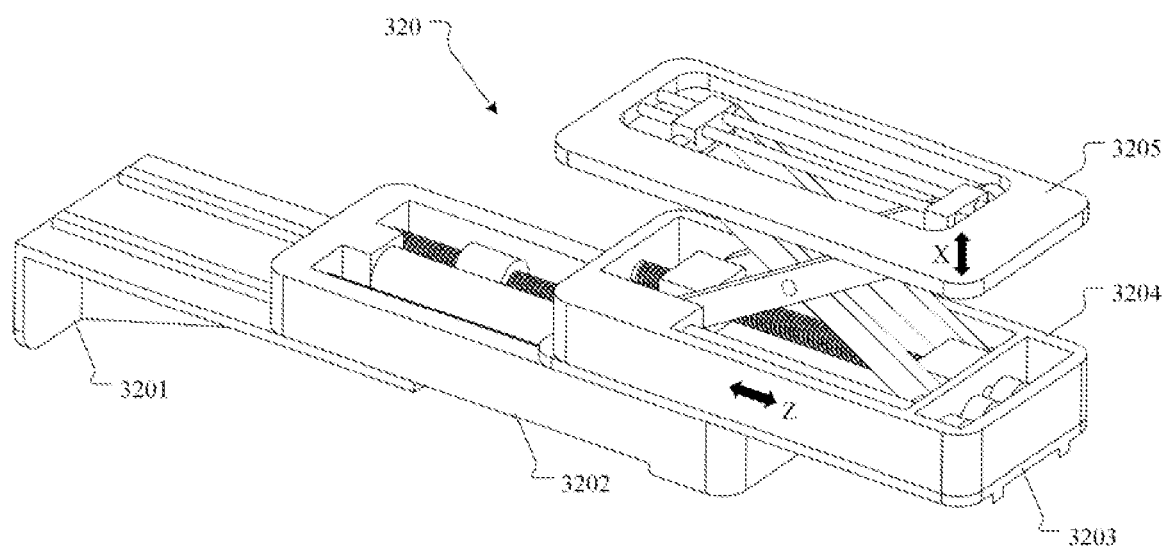
FIG. 23 shows a schematic diagram of the movement principle of the installation mechanism shown in FIG. 22.

FIG. 22 shows the three-dimensional structure of the installation mechanism 320 in one embodiment, and FIG. 23 shows the movement principle of the installation mechanism. As shown in FIG. 22 and FIG. 23, the installation mechanism 320 comprises an installation base 3201, a forward and backward driving unit 3202, and a translation drive unit 3204 successively arranged in a second direction X parallel to the plane of the instrument base 22. The installation base 3201 is fixed to the instrument base 22. The forward and backward driving unit 3202 is movably connected to the installation base 3201 and movably provided with a forward and backward pallet 3203. The forward and backward drive unit 3202 can move along a first direction Z perpendicular to the plane of the instrument base 22 and drive the forward and backward pallet 3203 to move along the first direction Z, thereby providing the instrument drive module 310 and the surgical instruments with a freedom of movement to move forward and backward along the first direction Z. The translation drive unit 3204 is fixedly connected to the forward and backward pallet 3203 and is movably provided with a translation pallet 3205. The translation drive unit 3204 can drive the translation pallet 3205 to move in the second direction X, thereby providing the instrument driving module and the surgical instrument with a degree of freedom to move along the second direction X.

The instrument drive module is fixedly connected to the translation pallet 3205. When the forward and backward drive unit 3202 and the translation drive unit 3204 work at the same time, the instrument drive module can be moved in space along the first direction Z, or along the second direction X, or their combined direction, thereby achieve the safe control of instruments with specific predefined configuration, while avoiding touching or affecting the posture adjustment reference point.

Figure 24:
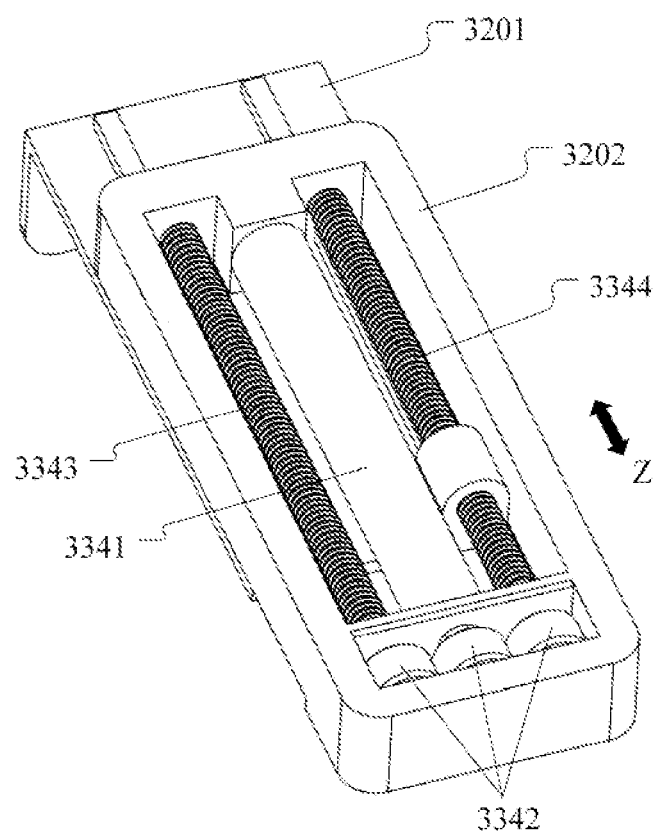
FIG. 24 and FIG. 25 show a schematic three-dimensional structural diagram of the forward and backward driving unit in an embodiment of the present invention.
Figure 25:
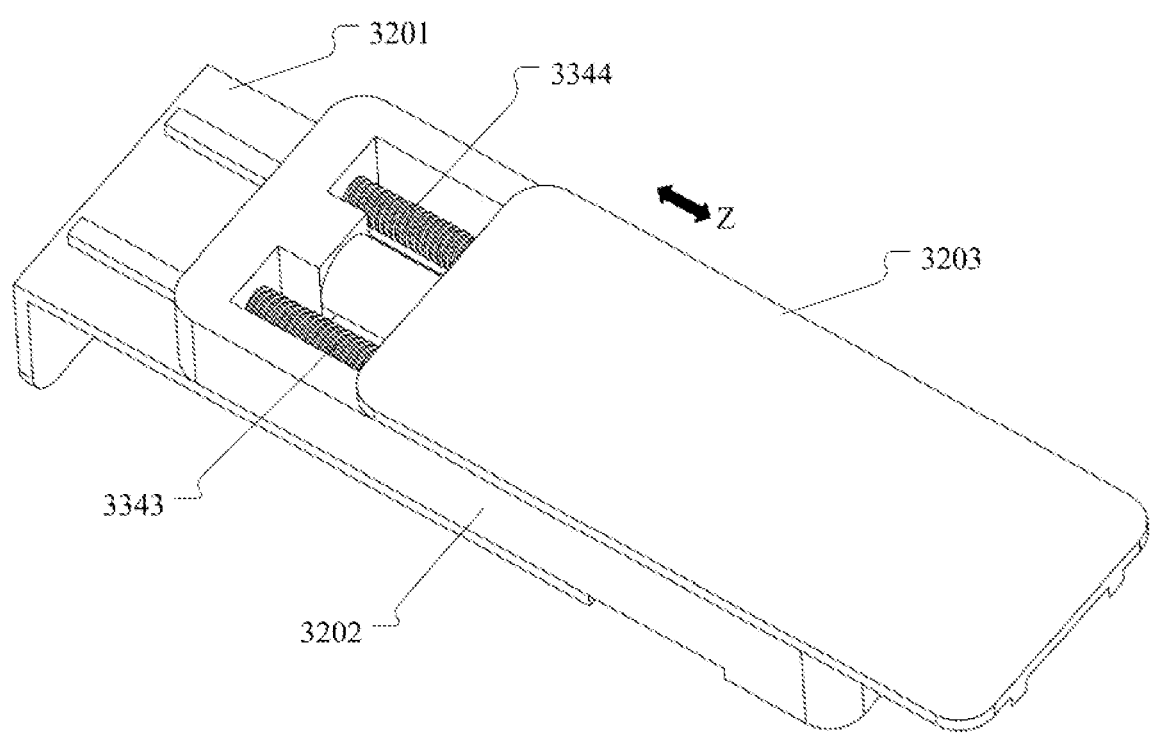

FIG. 24 and FIG. 25 show the three-dimensional structure of the forward and backward drive unit 3202 in an embodiment. Referring to FIG. 24 and FIG. 25, the forward and backward drive unit 3202 comprises a forward and backward drive motor 3341, which is provided with a first transmission gear set 3342, and a first lead screw 3343 as well as a second lead screw 3344, which are arranged side by side along the first direction Z with opposite rotation directions. The proximal end of the first lead screw 3343 (referring to the end close to the instrument base 22) is connected with the installation base 3201 in a matching manner. Specifically, it can be a connection of an inner threaded part and an outer threaded part in a matching manner. When the first lead screw 3343 rotates around its own axis, it can drive the forward and backward drive unit 3202 to move axially relative to the installation base 3201. The proximal end of the second lead screw 3344 is connected with the forward and backward pallet 3203 in a matching manner. Specifically, it can be a connection of an inner threaded part and an outer threaded part in a matching manner. When the second lead screw 3344 rotates around its own axis, it can drive the forward and backward pallet 3203 to move axially relative to the forward and backward drive unit 3202. The distal end of the first lead screw 3343 (referring to the end away from the instrument base 22) and the distal end of the second lead screw 3344 are driven by the first transmission gear set 3342. Since the rotation directions of the first lead screw 3343 and the second lead screw 3344 are contrary to each other, while driven by the same first transmission gear set 3342, so when the forward and backward driving motor 3341 rotates, the movement of the installation base 3201 relative to the forward and backward driving unit 3202 is contrary to the movement of the forward and backward pallet 3203 relative to the forward and backward driving unit 3202. Therefore, when the installation base 3201 is fixed to the instrument base 22, it is possible to provide a doubled movement stroke for the forward and backward pallet 3203 when the forward and backward drive motor 3341 rotates.

Specifically, as the forward and backward drive motor 3341 rotates forward, the first lead screw 3343 drives the forward and backward drive unit 3202 to advance along the first direction Z (moves away from the instrument base 22), and the second lead screw 3344 further drives the forward and backward pallet 3203 forward along the first direction Z. As the forward and backward drive motor 3341 reverses, the first lead screw 3343 drives the forward and backward drive unit 3202 to retreat along the first direction Z (moves toward the instrument base 22), and the second lead screw 3344 further drives the forward and backward pallet 3203 to retreat along the first direction Z. Due to the adoption of screw drives and the selection of appropriate thread angles, the forward and backward drive unit 3202 can achieve a self-lock when the system is powered off, keeping the current forward and backward position unchanged.

Figure 26:
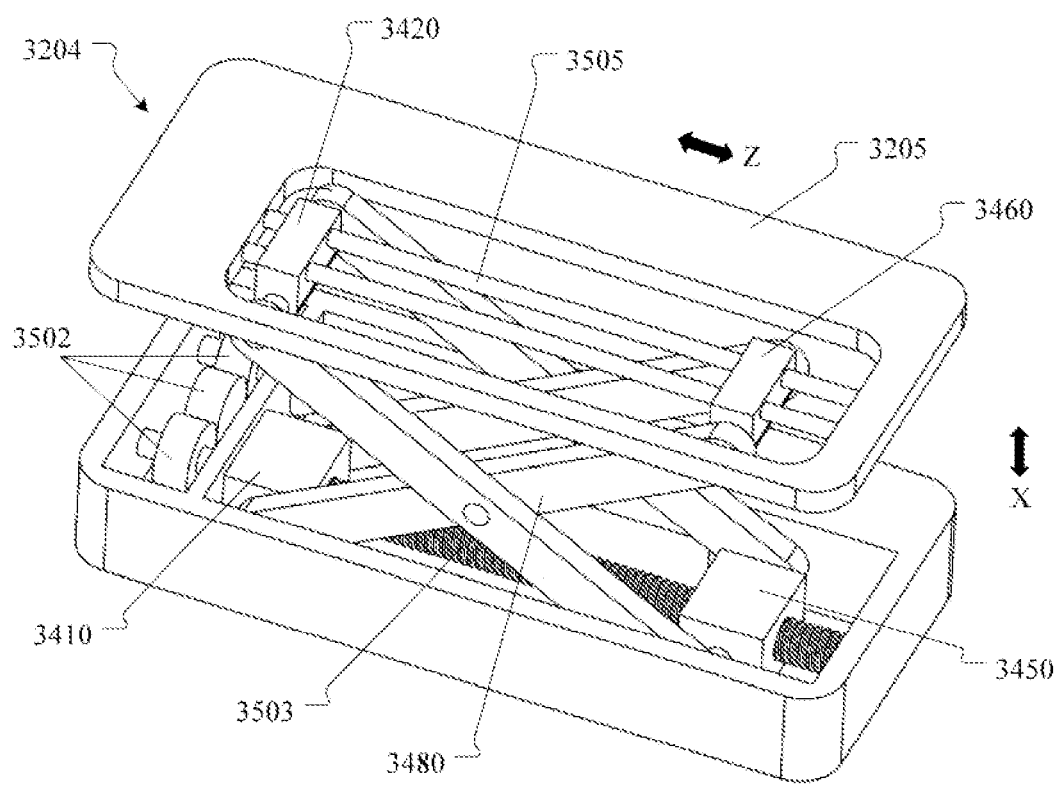
FIG. 26 to FIG. 28 show a schematic three-dimensional structural diagram of a translation drive unit in an embodiment of the present invention.
Figure 27:
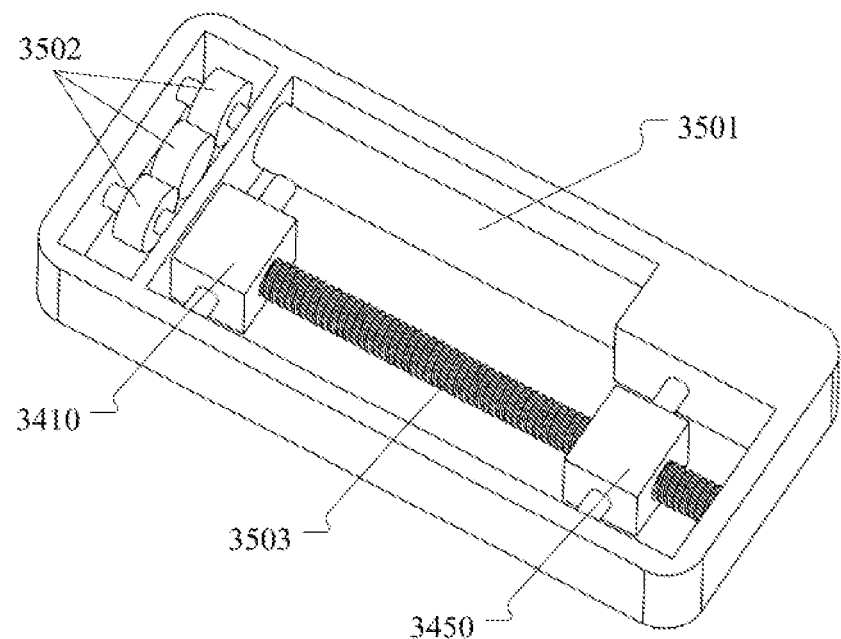
Figure 28:
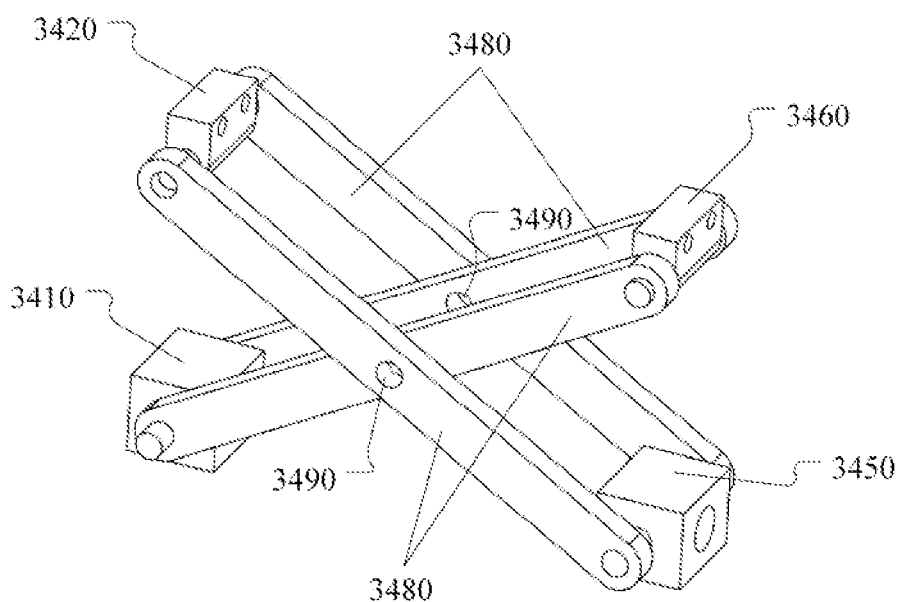

FIG. 26 to FIG. 28 show the three-dimensional structure of the translation drive unit 3204 in an embodiment. Referring to FIGS. 26 to 28, the translation drive unit 3204 comprises: a translation drive motor 3501, which is provided with a second transmission gear set 3502; and a drive screw 3503, arranged along the first direction Z and connected to the second transmission gear set 3502 at the proximal end. The second transmission gear set 3502 transmits a rotation motion from the translation drive motor 3501 to the drive screw 3503, and the rotation direction of the drive screw 3503 is consistent with the translation drive motor 3501. A pair of fixed hinges (comprising a lower fixed hinge 3410 and an upper fixed hinge 3420) are respectively fixed to the distal end of the drive screw 3503 and the distal end of a slide rail 3505 of the translation pallet 3205 arranged along the first direction Z. A pair of movable hinges (comprising a lower movable hinge 3450 and an upper movable hinge 3460) are respectively connected to the proximal end of the drive screw 3503 and the proximal end of the slide rail 3505. The drive screw 3503 and the lower movable hinge 3450 can be connected in a matching manner through an inner threaded part and an outer threaded part. When the drive screw 3503 rotates around its own axis, it can drive the lower movable hinge 3450 to move along its axis. The upper movable hinge 3460 is connected with the slide rail 3505 of the translation carriage 3205 in a matching manner.

The lower fixed hinge 3410, the lower movable hinge 3450, the upper fixed hinge 3420, and the upper movable hinge 3460 are cross-connected by two pairs of pivotable X-shaped supports 3480, and each pair of X-shaped supports 3480 intersects at an axis 3490. As the translation drive motor 3501 drives the drive screw 3503 to rotate, the pair of movable hinges 3450 and 3460 move along the drive screw 3503 and the slide rail 3505 respectively, the X-shaped support 3480 pivots, and the translation pallet 3205 moves along the second direction X. Specifically, when the drive screw 3501 rotates to drive the lower movable hinge 3450 to move along its axis, the angle of the pivotable X-shaped support 3480 changes, thereby achieving an upward or downward movement along the second direction X, while the upper movable hinge 3460 moves along the slide rail 3505. Thereby, the lifting and lowering of the translation pallet 3205 in the second direction X can be achieved. Due to the adoption of screw drives and the selection of appropriate thread angles, the translation drive unit 3204 can achieve a self-lock when powered off and can keep the current translation position unchanged.

Figure 29:
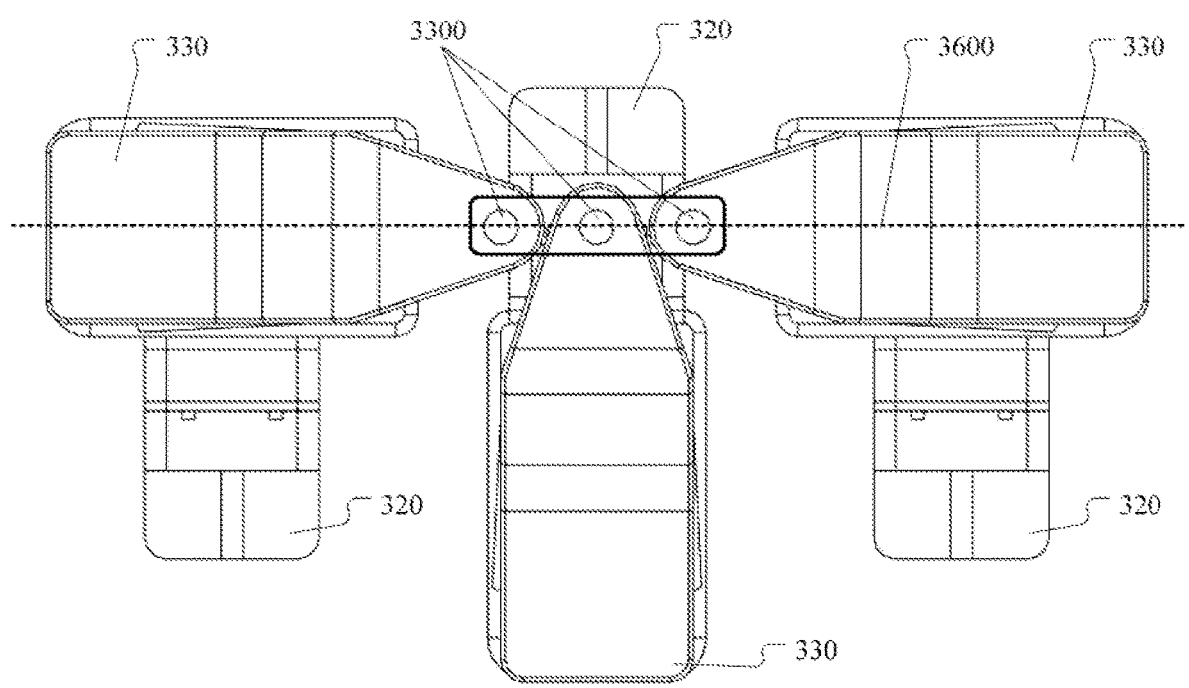
FIG. 29 shows a schematic view of the front position of a surgical instrument and installation mechanism in an embodiment of the present invention.

FIG. 29 shows the front view of a conventional surgical instrument and an installation mechanism 320 in an embodiment. A conventional surgical instrument refers to a surgical instrument whose end effector is coaxial with its instrument axis. Referring to FIG. 29, through the driving of the installation mechanism 320, the instrument shafts 3300 of the three surgical instruments 330 are aligned on a same horizontal line 3600 during operation, to ensure that the instrument shafts 3300 of the three surgical instruments 330 move in parallel.

Figure 30:
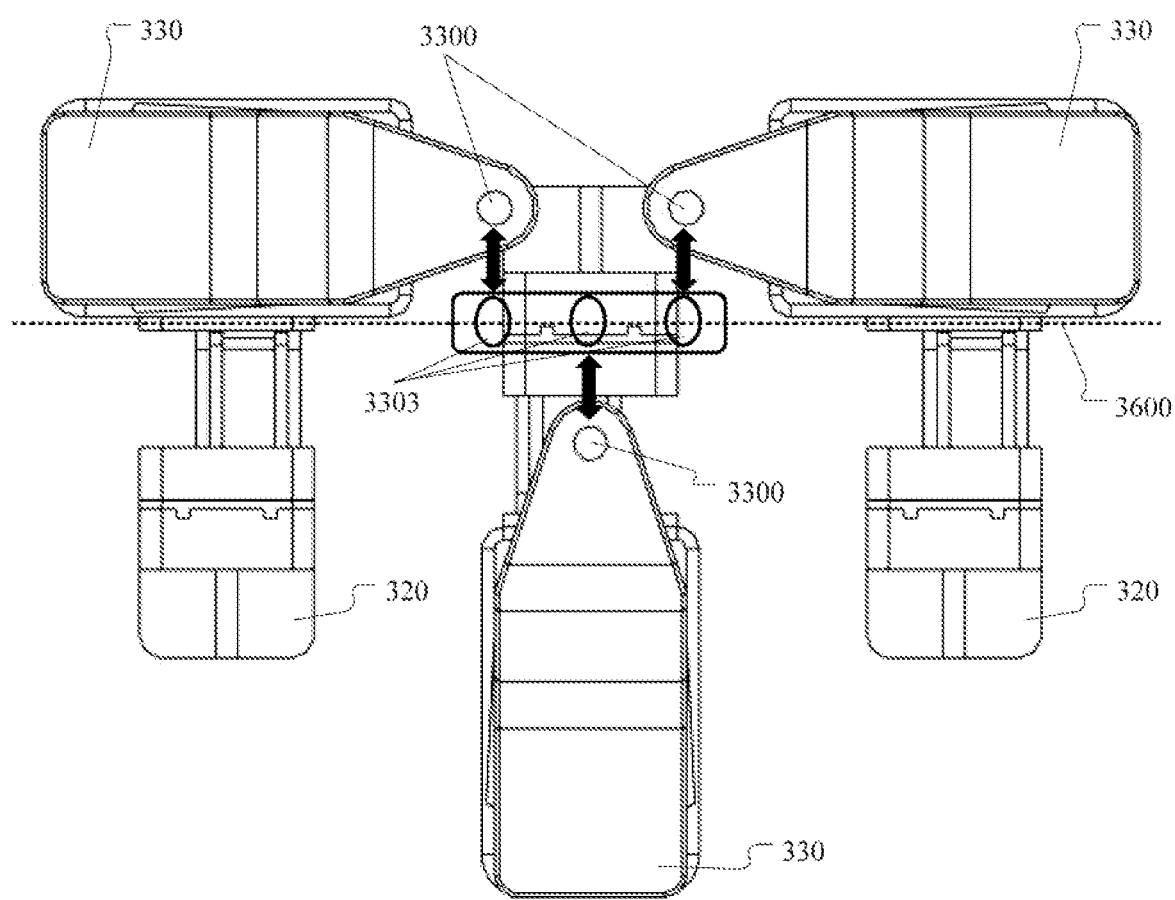
FIG. 30 shows a schematic view of the front position of another surgical instrument and installation mechanism in an embodiment of the present invention.
Figure 31:
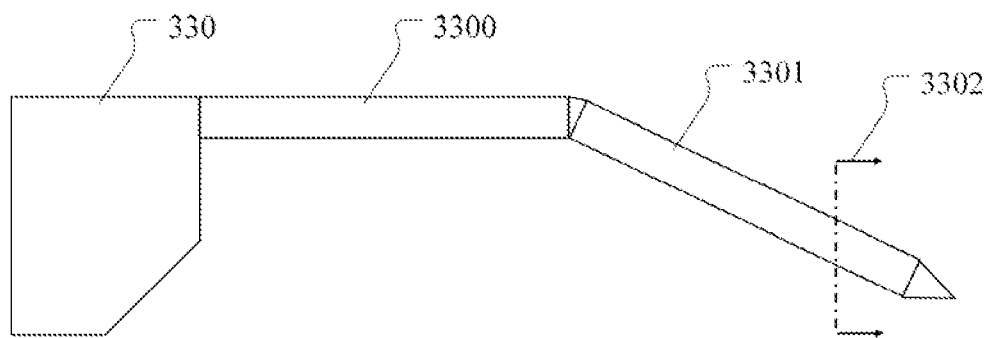
FIG. 31 shows a schematic diagram of the end effector of the surgical instrument shown in FIG. 30.

FIG. 30 shows the front view of surgical instruments with specific predefined configurations and the installation mechanisms 320 in one embodiment. FIG. 31 shows an end effector of a surgical instrument with specific predefined configuration. The surgical instrument with specific predefined configuration refers to an instrument with an end effector that is non-coaxial with its instrument shaft. As shown in FIG. 30 and FIG. 31, when the end effector 3301 of the surgical instrument 330 is non-coaxial with the instrument shaft 3300, in order to prevent the instrument shaft 3300 and the end effector 3301 from touching or affecting the posture adjustment reference point during movement, the forward and backward driving unit and the translation driving unit of the installation mechanism 320 can be operated simultaneously, so that the instrument driving module moves in the space along a combined direction of the above-mentioned first direction Z and second direction X, so as to achieve that the end effector 3301 of the surgical instrument 330 and the cross-section 3303 along section line 3302 remains at the same horizontal line 3600.

In summary, the robotic arm of the present invention can avoid movement interference or limited operating space when performing narrow-passage surgeries, and has degrees of freedom of spatial movement to meet the operation requirements for rough adjustment before the surgery and fine adjustment during minimally invasive surgeries such as single-port or few-port surgeries.

The above content is a further detailed description of the present invention in combination with specific preferred embodiments, and it cannot be concluded that the specific implementation of the present invention is limited to these descriptions. For those of ordinary skill in the technical field to which the present invention belongs, several simple deductions or substitutions can be made without departing from the concept of the present invention, and all of them should be regarded as belonging to the protection scope of the present invention.

The invention claimed is:

1. A robotic arm for minimally invasive surgery, characterized by comprising: a support mechanism, comprising a support base, and a distal end connected to the support base through a movable connector; and,
  a posture adjustment mechanism, comprising a rotation and pitching member rotatably connected to the distal end of the support mechanism, wherein, an instrument base is rotatably connected to an distal end of the rotation and pitching member, and, a first rotation axis of the rotation and pitching member intersects with a second rotation axis of the instrument base at a remote center of motion, and the rotation and pitching member is configured at least to drive the instrument base to perform a pitching movement relative to the remote center of motion;
and,
  an instrument driving mechanism, connected to the instrument base and used to install and drive one or more surgical instruments;
  wherein the rotation and pitching member comprises:
  a rotation base, connected to the distal end of the support mechanism through a first rotation joint, wherein the first rotation joint has a vertical rotation axis constituting the first rotation axis; and,
  a pitching assembly, provided with a proximal end movably connected to the rotation base and a distal end connected to the instrument base through a second rotation joint, wherein a rotation axis of the second rotation joint constitutes the second rotation axis;
  wherein the pitching assembly comprises:
  a pitch drive rod, provided with a first end connected to the rotation base through a first rotation mechanism; and,
  a first connecting rod, provided with a first end connected to a second end of the pitch drive rod through a second rotation mechanism; and,
  a second connecting rod, provided with a first end connected to a second end of the first connecting rod through a third rotation mechanism, and provided with a second end connected to the instrument base;
  wherein, the second rotation mechanism is parallel to and synchronously linked with the first rotation mechanism and the third rotation mechanism respectively; and when the first rotation mechanism drives the pitch drive rod to rotate, the second rotation mechanism drives the first connecting rod to translate, wherein an angle between the first connecting rod and the first rotation axis remains unchanged, and, the second rotation mechanism and the third rotation mechanism drive the second connecting rod to swing, wherein an angle between the second connecting rod and the pitch drive rod remains unchanged; and
  the first rotation mechanism comprises a first winch fixed on the rotation base, and an actuation shaft fixed on the first end of the pitch drive rod, wherein the actuation shaft is rotatably located at a center of the first winch; and,
  the second rotation mechanism comprises a second winch fixed on the first end of the first connecting rod, and a third winch rotatably connected to the second end of the pitch drive rod, wherein the second winch and the third winch share a passive shaft; and,
  the third rotation mechanism comprises a fourth winch fixed on the first end of the second connecting rod, and the fourth winch is rotatably connected to the second end of the first connecting rod, wherein a passive shaft of the fourth winch is parallel to the passive shaft of the second winch and the third winch as well as to the actuation shaft; and,
  the first winch, the second winch, the third winch, and the fourth winch are synchronously connected through coupling cables respectively.

2. The robotic arm of claim 1, wherein,
  the rotation base is configured as an L-shaped base, and an outer wall of a horizontal arm of the L-shaped base is connected to the support mechanism; and,
  the pitching assembly is connected to an inner wall of a vertical arm of the L-shaped base, and rotation axes of the first rotation mechanism, the second rotation mechanism and the third rotation mechanism are all configured as horizontal rotation axes.

3. The robotic arm of claim 1, wherein,
  the instrument driving mechanism comprises a plurality of instrument driving modules arranged in a parallel configuration, which are respectively connected to the instrument base through a plurality of installation mechanisms, and the installation mechanisms are configured to drive the instrument driving modules to move perpendicular and/or parallel to a plane of the instrument base, and movement paths of the instrument driving modules do not interfere with each other.

4. The robotic arm of claim 3, wherein, sequentially arranged along a second direction parallel to the plane of the instrument base, each of the installation mechanisms comprises:
  an installation base, fixed to the instrument base; and,
  a forward and backward drive unit, movably connected to the installation base and movably connected with a forward and backward pallet, wherein the forward and backward drive unit is configured to move along a first direction perpendicular to the plane of the instrument base and to drive the forward and backward pallet along the first direction; and,
  a translation drive unit, fixedly connected to the forward and backward pallet and movably connected to a translation pallet, wherein the translation drive unit is configured to drive the translation pallet to move in the second direction, and the instrument drive module is fixedly connected to the translation pallet.

5. The robotic arm according to claim 4, wherein the forward and backward driving unit comprises:
  a forward and backward drive motor, equipped with a first transmission gear set; and,
  a first lead screw and a second lead screw, respectively with opposite rotation directions, and arranged side by side along the first direction;
  wherein a proximal end of the first lead screw is connected in a matching manner to the installation base, and a proximal end of the second lead screw is connected in a matching manner to the forward and backward pallet, and a distal end of the first lead screw and a distal end of the second lead screw are driven by the first transmission gear set; and,
  when the forward and backward driving motor rotates forward, the first lead screw drives the forward and backward driving unit to move forward in the first direction, and the second lead screw drives the forward and backward pallet to move forward in the first direction; and, when the forward and backward driving motor reverses, the first lead screw drives the forward and backward driving unit to move backward along the first direction, and the second lead screw drives the forward and backward pallet to move backward along the first direction.

6. The robotic arm of claim 4, wherein the translation drive unit comprises:
   a translation drive motor, equipped with a second transmission gear set; and,
   a drive screw, arranged along the first direction and connected to a distal end of the second transmission gear set; and,
   a pair of fixed hinges, respectively fixed to the distal end of the drive screw and a distal end of a slide rail provided at the translation pallet along the first direction; and,
   a pair of movable hinges, respectively connected to the proximal end of the drive screw and the proximal end of the slide rail;
   wherein the pair of fixed hinges and the pair of movable hinges are connected by a pivotable X-shaped support; and,
   when the translation drive motor drives the drive screw to rotate, the movable hinges respectively move along the drive screw and the slide rail, and the X-shaped support pivots, and the translation pallet moves along the second direction.

7. The robotic arm of claim 1, wherein the movable connector comprises:
   a vertical support rod, connected to the support base through a first sliding joint, wherein the first sliding joint is configured to drive the vertical support rod to move vertically; and,
   a planar rod assembly, connected to the vertical support rod through a first bearing rotation joint, wherein the first bearing rotation joint is configured to drive the planar rod assembly to rotate in a plane perpendicular to the vertical support rod, and a distal end of the planar rod assembly constitutes the distal end of the support mechanism.

8. The robotic arm of claim 7, wherein,
   the planar rod assembly comprises: a first rod, connected to the vertical support rod through the first bearing rotation joint, and, a second rod, connected through a second bearing rotation joint to the first rod; or,
   the planar rod assembly comprises: a third rod, connected to the vertical support rod through the first bearing rotation joint, and, a fourth rod, connected to the third rod through a second sliding joint.

9. The robotic arm of claim 1, wherein,
   the instrument driving mechanism comprises a plurality of instrument driving modules arranged in a parallel configuration, which are respectively connected to the instrument base through a plurality of installation mechanisms, and the installation mechanisms are configured to drive the instrument driving modules to move perpendicular and/or parallel to a plane of the instrument base, and movement paths of the instrument driving modules do not interfere with each other.

10. The robotic arm of claim 9, wherein, sequentially arranged along a second direction parallel to the plane of the instrument base, each of the installation mechanisms comprises:

an installation base, fixed to the instrument base; and,
a forward and backward drive unit, movably connected to the installation base and movably connected with a forward and backward pallet, wherein the forward and backward drive unit is configured to move along a first direction perpendicular to the plane of the instrument base and to drive the forward and backward pallet along the first direction; and,
a translation drive unit, fixedly connected to the forward and backward pallet and movably connected to a translation pallet, wherein the translation drive unit is configured to drive the translation pallet to move in the second direction, and the instrument drive module is fixedly connected to the translation pallet.

11. The robotic arm according to claim 10, wherein the forward and backward driving unit comprises:
   a forward and backward drive motor, equipped with a first transmission gear set; and,
   a first lead screw and a second lead screw, respectively with opposite rotation directions, and arranged side by side along the first direction;
   wherein a proximal end of the first lead screw is connected in a matching manner to the installation base, and a proximal end of the second lead screw is connected in a matching manner to the forward and backward pallet, and a distal end of the first lead screw and a distal end of the second lead screw are driven by the first transmission gear set; and,
   when the forward and backward driving motor rotates forward, the first lead screw drives the forward and backward driving unit to move forward in the first direction, and the second lead screw drives the forward and backward pallet to move forward in the first direction; and,
   when the forward and backward driving motor reverses, the first lead screw drives the forward and backward driving unit to move backward along the first direction, and the second lead screw drives the forward and backward pallet to move backward along the first direction.

12. The robotic arm of claim 10, wherein the translation drive unit comprises:
   a translation drive motor, equipped with a second transmission gear set; and,
   a drive screw, arranged along the first direction and connected to a distal end of the second transmission gear set; and,
   a pair of fixed hinges, respectively fixed to the distal end of the drive screw and a distal end of a slide rail provided at the translation pallet along the first direction; and,
   a pair of movable hinges, respectively connected to the proximal end of the drive screw and the proximal end of the slide rail;
   wherein the pair of fixed hinges and the pair of movable hinges are connected by a pivotable X-shaped support; and,
   when the translation drive motor drives the drive screw to rotate, the movable hinges respectively move along the drive screw and the slide rail, and the X-shaped support pivots, and the translation pallet moves along the second direction.

13. The robotic arm of claim 1, wherein the movable connector comprises:

a vertical support rod, connected to the support base through a first sliding joint, wherein the first sliding joint is configured to drive the vertical support rod to move vertically; and, a planar rod assembly, connected to the vertical support rod through a first bearing rotation joint, wherein the first bearing rotation joint is configured to drive the planar rod assembly to rotate in a plane perpendicular to the vertical support rod, and a distal end of the planar rod assembly constitutes the distal end of the support mechanism.

14. The robotic arm of claim 13, wherein, the planar rod assembly comprises: a first rod, connected to the vertical support rod through the first bearing rotation joint, and, a second rod, connected through a second bearing rotation joint to the first rod; or, the planar rod assembly comprises: a third rod, connected to the vertical support rod through the first bearing rotation joint, and, a fourth rod, connected to the third rod through a second sliding joint.

15. A robotic arm for minimally invasive surgery, characterized by comprising:

a support mechanism, comprising a support base, and a distal end connected to the support base through a movable connector; and, a posture adjustment mechanism, comprising a rotation and pitching member rotatably connected to the distal end of the support mechanism, wherein, an instrument base is rotatably connected to a distal end of the rotation and pitching member, and, a first rotation axis of the rotation and pitching member intersects with a second rotation axis of the instrument base at a remote center of motion, and the rotation and pitching member is configured at least to drive the instrument base to perform a pitching movement relative to the remote center of motion; and an instrument driving mechanism, connected to the instrument base and used to install and drive one or more surgical instruments;

wherein the rotation and pitching member comprises:

a fixed base, fixed to the distal end of the support mechanism; and, a rotation and pitching chain, comprising a drive rod connected to the fixed base through a proximal rotation actuator, and a passive rod group connected to the drive rod through a passive rotation joint;

wherein, the proximal rotation actuator has a vertical rotation axis, which constitutes the first rotation axis, and, a distal end of the passive rod group is connected to the instrument base through a distal rotation actuator, and a rotation axis of the distal rotation actuator constitutes the second rotation axis; and the passive rod group comprises a plurality of passive rods connected through passive rotation joints; and, the rotation and pitching chain comprises a first winch, wherein the first winch is fixed to the fixed base and is coaxial with the proximal rotation actuator; and, the passive rotation joint between the passive rod group and the drive rod comprises a second winch fixed on a proximal end of a first passive rod, and a third winch rotatably connected to a distal end of the drive rod, wherein the second winch and the third winch share a passive shaft; and, the passive rotation joint between the first passive rod and a second passive rod comprises a fourth winch fixed on a proximal end of the second passive rod, and the fourth winch is rotatably connected to the second end of the first passive rod, wherein a passive shaft of the fourth winch, the passive shaft of the second winch, and a shaft of the proximal rotation actuator are respectively colinear with the remote center of motion; and, the first winch, the second winch, the third winch, and the fourth winch are synchronously connected through coupling cables respectively.

16. The robotic arm of claim 15, wherein, the rotation and pitching chain comprises a plurality of drive rods, a plurality of passive rod groups, a plurality of proximal rotation actuators, and a plurality of passive rotation joints; and the rotation and pitching chain has a plurality of parallel branch chains, and each of the branch chains comprises a drive rod and a passive rod group connected to each other.

17. The robotic arm of claim 16, wherein the rotation and pitch chain comprises:

a first branch chain of the branch chains, comprising a first drive rod of the drive rods, connected to the fixed base through a first proximal rotation actuator of the proximal rotation actuators, and a first passive rod group of the passive rod groups, connected to the first drive rod through a first passive rotation joint of the passive rotation joints, wherein the first passive rod group comprises a plurality of first passive rods connected through passive rotation joints; and, a second branch chain of the branch chains, comprising a second drive rod of the drive rods connected to the fixed base through a second proximal rotation actuator of the proximal rotation actuators, and a second passive rod group of the passive rod groups connected to the second drive rod through a second passive rotation joint of the passive rotation joints, wherein the second passive rod group comprises a plurality of second passive rods connected through passive rotation joints;

wherein the first proximal rotation actuator and the second proximal rotation actuator are coaxial with the first rotation axis and are configured to be actuated jointly or independently, and the distal end of the first passive rod group and the distal end of the second passive rod group are jointly connected to the instrument base through the distal rotation actuator.

18. The robotic arm of claim 17, wherein, the first passive rod group comprises two first passive rods and the second passive rod group comprises two second passive rods, and, a proximal first passive rod of the first passive rod group and a proximal second passive rod of the second passive rod group are connected through an intermediate rotation axis, wherein the intermediate rotation axis intersects with the first rotation axis.

19. The robotic arm of claim 17, wherein, projections on a vertical plane of the first drive rod, of each of the first passive rods, of the second drive rod, and of each of the second passive rods are all arcs with a same radius of curvature.

* * * * *